(12) United States Patent
Kubota

(10) Patent No.: US 8,053,483 B2
(45) Date of Patent: Nov. 8, 2011

(54) GAS ADSORBENT

(75) Inventor: Hirohisa Kubota, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 785 days.

(21) Appl. No.: 12/063,154

(22) PCT Filed: Aug. 10, 2006

(86) PCT No.: PCT/JP2006/315855
§ 371 (c)(1),
(2), (4) Date: Feb. 27, 2008

(87) PCT Pub. No.: WO2007/018266
PCT Pub. Date: Feb. 15, 2007

(65) Prior Publication Data
US 2009/0227693 A1 Sep. 10, 2009

(30) Foreign Application Priority Data

| Aug. 10, 2005 | (JP) | 2005-232625 |
| Aug. 10, 2005 | (JP) | 2005-232648 |
| Aug. 10, 2005 | (JP) | 2005-232655 |
| Oct. 12, 2005 | (JP) | 2005-298214 |
| Aug. 4, 2006 | (JP) | 2006-213977 |

(51) Int. Cl.
*B01J 41/00* (2006.01)
(52) U.S. Cl. ............. 521/29; 422/4; 422/122; 502/401; 502/402
(58) Field of Classification Search .................... 521/29; 422/4, 122; 502/402, 401
See application file for complete search history.

(56) References Cited

U.S. PATENT DOCUMENTS

| 4,300,577 | A | | 11/1981 | Horsewell et al. |
| 4,675,309 | A | * | 6/1987 | Hirai et al. ................... 502/402 |
| 5,447,701 | A | * | 9/1995 | Inoue et al. ................... 423/224 |
| 7,018,538 | B2 | * | 3/2006 | Leiser et al. ................... 210/635 |
| 2001/0043881 | A1 | * | 11/2001 | Wagner et al. ................... 422/4 |

FOREIGN PATENT DOCUMENTS

| JP | 54-151200 | | 11/1979 |
| JP | 06-190235 | * | 7/1994 |
| JP | 6-190235 | | 7/1994 |
| JP | 2001 38202 | | 2/2001 |
| JP | 2001-038202 | * | 2/2001 |

(Continued)

OTHER PUBLICATIONS

Office Action issued Feb. 11, 2011, in China Patent Application No. 200680028016.7 (witn English translation).

*Primary Examiner* — Peter D. Mulcahy
*Assistant Examiner* — Henry Hu
(74) *Attorney, Agent, or Firm* — Oblon, Spivak, McClelland, Maier & Neustadt, L.L.P.

(57) ABSTRACT

A gas adsorbent which has sufficient gas adsorptivity for noxious gas components in a cigarette when brought into contact with a gas stream having a high flow rate as that when it passes through a cigarette filter, and which releases a small amount of bad odor components such as amine impurities and free noxious components which adversely affect health such as aromatic compounds derived from the gas adsorbent itself, the gas adsorbent satisfying conditions (I), (II), (IV) and (V) or conditions (I), (III), (IV) and (V), as described in the specification.

8 Claims, 1 Drawing Sheet

FOREIGN PATENT DOCUMENTS

| | | | |
|---|---|---|---|
| JP | 2002-052340 | * | 2/2002 |
| JP | 2002 52340 | | 2/2002 |
| JP | 2002-528106 | | 9/2002 |
| JP | 2004-538016 | | 12/2004 |
| JP | 2005 103403 | | 4/2005 |
| JP | 2005-103403 | * | 4/2005 |
| WO | WO 00/25611 | | 5/2000 |
| WO | WO 03/015544 A1 | | 2/2003 |
| WO | WO-2007/018266 A1 | * | 2/2007 |

* cited by examiner

GAS ADSORBENT

TECHNICAL FIELD

The present invention relates to a gas adsorbent to be used for a gas filter or an apparatus for removal of noxious gas. It relates to a gas adsorbent suitably used for removal of noxious gas contained in building material, odor emitted in the cooking place, a filter for a muffler for an automobile, a deodorant in the car interior, in a room or in a bath room, or removal of noxious gas and odor components in a sewage plant, a waste incineration plant, a garbage truck, a waste truck, a collection cabinet, an air conditioner, a refrigerator, the furniture, a cushion, a stuffed toy, disposable diapers, a sewerage pipe or sewerage works, particularly for a cigarette filter or a gas filter of apparatus which is required to remove noxious gas in cigarette smoke such as an air cleaner or a car air conditioner.

BACKGROUND ART

In recent years, along with great development of living environment, a very small amount of chemical substances present in life space increasingly attract attention as causes of environmental pollution, endocrine disrupting chemicals (environmental hormones) and chemical sensitivity.

On the other hand, when a cigarette burns, it generates a granular phase and a vapor phase in its smoke, and the vapor phase contains, for example, carbon monoxide, nitrogen oxide (NOx) and ammonia and in addition, noxious substances including carbonyl compounds and organic acids, phenol derivatives such as phenol, cresol and catechol, hydrogen cyanide, sulfides represented by hydrogen sulfide, etc. Among them, carbonyl compounds attract attention as main causative substances of chemical sensitivity in recent years and are known as chemical substances harmful to the human body.

Here, carbonyl compounds are compounds having a carbonyl group (C=O) such as aldehydes and ketones. They are one of noxious gas components which are highly likely to be present in the living environment. For example, a low molecular aliphatic aldehyde is a major component among various noxious gas components contained in the cigarette smoke, and further, formaldehyde has been known as a major causative component of sick house syndrome, emitted from building material in recent years. Among noxious gas components contained in a cigarette, as carbonyl compounds, formaldehyde, acetaldehyde, acrolein, propionaldehyde, butylaldehyde, crotonaldehyde, acetone, methyl ethyl ketone, a benzaldehyde derivative of an aromatic aldehyde compound, etc. have been reported.

In order to remove such noxious gas components thereby to maintain a pleasant living environment, a gas adsorbent having high adsorptivity for noxious gas components has been required, and various gas adsorbents have been used in home life.

In general, for many of gas adsorbents, porous materials which adsorb gas in their physically porous structures, such as activated carbon, silica gel and zeolite have been widely used. However, among such porous materials, for example, silica gel easily adsorbs noxious substances such as carbonyl compounds and hydrogen cyanide but easily releases the adsorbed components as well, and is thereby known as an adsorbent having low retention properties for such noxious substances (having low adsorptivity).

Further, in a case where a gas stream having a flow rate at the same level as that when it passes through a cigarette filter is brought into contact with the surface of the porous material such as activated carbon, silica gel or zeolite, the gas adsorptivity tends to be low as compared with a case where a gas stream having a relatively low flow rate is made to pass.

The flow rate of a gas stream which passes through a cigarette filter at the time of smoking is very high, and it has been known that the flow rate is approximately from 10 to 30 m/sec and the retention time is within one second. Accordingly, when a gas adsorbent is used in a cigarette filter, it is required to have a sufficient gas adsorptivity for a gas stream having a flow rate at the time of passing through the cigarette filter. Further, also when a gas adsorbent is used not for a cigarette filter but for a gas filter of apparatus which is required to remove noxious gas in cigarette smoke such as an air cleaner or a car air conditioner, it is desired to have a sufficient gas adsorptivity for a high flow rate gas stream with a view to improving the capacity.

Patent Document 1 discloses a cigarette filter comprising a non-volatile inorganic substrate having a reactive functional group as a reagent, therein the reagent chemically reacts with a gaseous component of a smoke stream to remove the gaseous component from the smoke stream.

Patent Document 1 proposes a cigarette filter containing a silica gel having 3-aminopropylsilyl groups as the most preferred embodiment of the reagent, and that primary amino groups in the 3-aminopropylsilyl groups chemically react with and covalently bonded to noxious substances such as hydrogen cyanide and aldehydes thereby to selectively remove them. However, the cigarette filter containing the silica gel has a low amino group content, whereby its adsorption amount of noxious substances such as hydrogen cyanide is insufficient, and aldehydes are not likely to be removed. Further, in preparation of a silica gel to which propylsilyl groups are bonded as a gas adsorbent from 3-aminopropyltriethoxysilane and silica gel, unreacted 3-aminopropyltriethoxysilane will remain. The obtained gas adsorbent is dried in an oven, and if unreacted 3-aminopropyltriethoxysilane remains in a large amount in the gas adsorbent, the gas adsorbent will emit an amine odor even after drying and may influence the odor and the flavor.

On the other hand, it has been studied to use an ion exchange resin as a gas adsorbent so as to remove noxious substances. For example, Patent Document 2 discloses a multiple section cigarette filter comprising a selective adsorbent section comprising a selective adsorbent material having an affinity for a predetermined class of chemical compounds dispersed throughout a fibrous material; and a general adsorbent section comprising a general adsorbent material having a high surface area and being capable of adsorbing smoke constituents without a high degree of specificity, the selective adsorbent section and the general adsorbent section being co-axially aligned in tandem. Patent Document 2 proposes use of activated coconut carbon as the general adsorbent material having a large surface area and capable of adsorbing smoke constituents without a high degree of specificity, and Duolite A7 (tradename, manufactured by Rohm and Haas) as the selective adsorbent material having an affinity for the chemical compounds.

Duolite A7 has a phenol-formaldehyde resin matrix and is surface-functionalized with primary and secondary amine groups, thereby enhancing the resin's specificity toward the aldehydes. However, for the Duolite A7, a phenol derivate is used to form the resin skeleton, and accordingly free noxious components such as an aromatic compound derived therefrom are released. Further, according to the experimental results disclosed in Patent Document 2, the adsorption amount of acetaldehyde is not good.

Patent Document 3 discloses a cigarette filter comprising a first component which is a quick adsorbent for gaseous components in cigarette smoke containing aldehydes with low retention properties, and a second component which includes aminos and which is chemically bonded to the gaseous components to generate a substantially non-volatile reaction product, mixed or very closely dispersed. Patent Document 3 discloses, as specific examples of the second component, Duolite A7 (tradename) disclosed in Patent Document 2 also and an amino group type anion exchange resin such as DIAION CR20 (tradename, manufactured by Mitsubishi Chemical Corporation) as well.

Further, Patent Document 4 discloses a gas adsorbent which is a crosslinked polymer mainly comprising a vinylamine of which the nitrogen atom may be alkylated and a polyvinyl compound. The gas adsorbent in Patent Document 4 is a gas adsorbent which is a vinylamine type ion exchange resin comprising an aromatic divinyl compound as a crosslinkable component and which contains a vinylamine component which is directly related to gas adsorption power in a large amount.

A gas adsorbent comprising DIAION CR20 (tradename, manufactured by Mitsubishi Chemical Corporation) disclosed in Patent Document 3 and a vinylamine type ion exchange resin disclosed in Patent Document 4 is intended to increase adsorptivity for aldehydes, but such a gas adsorbent is an amino group type anion exchange resin, and amine impurities released therefrom make an amine odor, thus significantly influences the odor and the flavor. Further, since styrene or a divinylbenzene compound is used as e.g. a crosslinkable component, a free noxious component such as an aromatic compound derived therefrom is released.

Further, Patent Document 4 also discloses a process of removing an acidic gas from a gas containing an acidic gas, which comprises bringing it into contact with the gas containing an acidic gas to adsorb the acid gas, and then heating the gas adsorbent in which the acidic gas is adsorbed to disorb the acidic gas.

However, by the above process, release of the above free noxious components and amine impurities can not sufficiently be suppressed, and further, if washing with a basic aqueous solution is carried out, even amino groups in the gas adsorbent are removed, thus decreasing the effect of the gas adsorbent. Further, if washing with an acid or an alkali is carried out, formalin will form, which will remain in a vinylamine ion exchange resin to be finally obtained. It is very difficult to solve the above problems and to realize industrial mass production by the process disclosed in Patent Document 4.

Further, as described above, in general, for many of gas adsorbents to be used for a cigarette filter, porous materials which adsorb gas in their physical porous structures, such as activated carbon, silica gel and zeolite have been widely used. However, if such a porous gas adsorbent is used for a cigarette filter by itself, since adsorption selectivity is low, not only aimed is noxious gas components but also flavorous components useful for a cigarette such as nicotinamide originally contained in a cigarette or 1-menthol to be added to a cigarette are adsorbed, thus impairing the flavor of the cigarette. Accordingly, a gas adsorbent which will not impair flavorous components is desired for a cigarette.

Patent Document 1: JP-A-2002-528106

Patent Document 2: JP-A-2004-538016

Patent Document 3: JP-A-54-151200

Patent Document 4: JP-A-6-190235

DISCLOSURE OF THE INVENTION

Objects to be Accomplished by the Invention

The object of the present invention is to provide a gas adsorbent which exhibits a sufficient gas adsorptivity for noxious gas components in a cigarette when brought into contact with a gas stream having a high flow rate as that when it passes through a cigarette filter, and which is less likely to release bad odor components such as amine impurities and free noxious components which adversely affect health such as an aromatic compound derived from the gas adsorbent itself.

Further, another object of the present invention is to provide a gas adsorbent which is less likely to adsorb flavorous components useful for a cigarette such as nicotinamide originally contained in cigarette smoke and 1-menthol to be added to a cigarette, which can selectively and effectively remove acidic noxious components such as hydrogen cyanide, and which is less likely to release components which adversely affect the flavor such as amine impurities and free noxious components which adversely affect health such as an aromatic compound derived from the gas adsorbent itself.

Means to Accomplish the Objects

The present inventor has conducted extensive studies to accomplish the above objects and as a result, found the following. Namely, in order that a gas adsorbent efficiently absorbs noxious components contained in a gas stream having a high flow rate, particularly the mean pore radius should be relatively large, and in addition, the amount of release of bad odor components such as amine impurities and free noxious components such as an aromatic compound and the neutral salt decomposition capacity should be predetermined amounts or below. Further, he had found that in addition to the above concept of the mean pore radius, when the acid adsorption capacity is required to be a predetermined amount or more, the effect of adsorbing noxious components is further increased.

He has further found that a gas adsorbent of which the amounts of adsorption of the respective noxious component derived from a cigarette out of the system and the gas adsorbent are respectively lower than values determined by a specific evaluation method, is excellent as a gas adsorbent.

Further, he has found that in a case where a gas adsorbent is used for a cigarette filter, one having an adsorption amount of flavorous components useful for a cigarette lower than a value determined by a specific evaluation method and a noxious component adsorption amount lower than a value determined by a specific evaluation method is excellent as a gas adsorbent.

Namely, the present invention provides the following gas adsorbent.

[1] A gas adsorbent according to a first aspect of the present invention

A gas adsorbent which satisfies the following conditions (I), (II), (IV) and (V) or the following conditions (I), (III), (IV) and (V):

(I) the mean pore radius of the gas adsorbent is at least 330 Å and at most 3,000 Å as measured by a mercury porosimeter;

(II) the amine elution amount from the gas adsorbent per unit mass is at most 10 μeq/g;

(III) the content of a monocyclic aromatic compound represented by the following formula 1 in the gas adsorbent per unit mass is at most 4 mg/g:

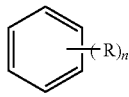

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different;

(IV) the neutral salt decomposition capacity is at most 0.43 meq/g; and (V) the acid adsorption capacity of the gas adsorbent per unit mass is at least 1.5 meq/g.

[2] A gas adsorbent according to a second aspect of the present invention

A gas adsorbent which satisfies the following conditions (VI) and (VII):

(VI) the adsorption amount of propionaldehyde in the gas adsorbent per unit mass is at least 240 mg/g as measured by using a 2 wt % propionaldehyde aqueous solvent solution; and (VII) the content of a monocyclic aromatic compound represented by the following formula 1 in the gas adsorbent per unit mass is at most 5 µg/g:

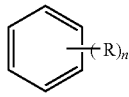

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different.

[3] A gas adsorbent according to a third aspect of the present invention

A gas adsorbent which satisfies the following conditions (VIII) and (IX):

(VIII) the adsorption amount of propionaldehyde in the gas adsorbent per unit mass is at least 330 mg/g as measured by using a 2 wt % propionaldehyde aqueous solvent solution; and (IX) the amine elution amount from the gas adsorbent per unit mass is at most 10 µeq/g.

[4] A Gas Adsorbent According to a Fourth Aspect of the Present Invention

A gas adsorbent which satisfies the following conditions (X) and (VII):

(X) after 100.0 ml of a propionaldehyde 100 ppm aqueous solution at 25° C. is brought into contact with 5 g of the gas adsorbent and left for 3 minutes, the concentration of the propionaldehyde aqueous solution is at most 80 ppm; and (VII) the content of a monocyclic aromatic compound represented by the following formula 1 in the gas adsorbent per unit mass is at most 5 µg/g:

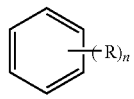

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different.

[5] A gas adsorbent according to a fifth aspect of the present invention

A gas adsorbent which satisfies the following conditions (X) and (IX):

(X) after 100.0 ml of a propionaldehyde 100 ppm aqueous solution at 25° C. is brought into contact with 5 g of the gas adsorbent and left for 3 minutes, the concentration of the propionaldehyde aqueous solution is at most 80 ppm; and (IX) the amine elution amount from the gas adsorbent per unit mass is at most 10 µeq/g.

[6] A gas adsorbent according to a sixth aspect of the present invention

A gas adsorbent which satisfies the following conditions (XI) and (XII) and/or the following conditions (XI) and (XIII), and which is used as a component of forming a cigarette filter:

(XI) the amine elution amount from the gas adsorbent per unit mass is at most 10 µeq/g, and the acid adsorption capacity of the gas adsorbent per unit mass is at least 2.5 meq/g;

(XII) the adsorption amount of nicotinamide in the gas adsorbent per unit mass is at most 10 mg/g as measured by using a 1 wt % nicotinamide aqueous solution; and (XIII) the adsorption amount of 1-menthol in the gas adsorbent per unit mass is at most 50 mg/g as measured by using a 2 wt % 1-menthol aqueous solution based on a 50 wt % methanol aqueous solution.

[7] A gas adsorbent according to a seventh aspect of the present invention

A gas adsorbent which satisfies the following conditions (XIV) and (XII) and/or the following conditions (XIV) and (XIII), and which is used as a component of forming a cigarette filter:

(XIV) the content of a monocyclic aromatic compound represented by the following formula 1 in the gas adsorbent per unit mass is at most 10 µg/g, and the acid adsorption capacity of the gas adsorbent per unit mass is at least 2.5 meq/g:

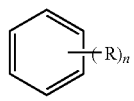

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different;

(XII) the adsorption amount of nicotinamide in the gas adsorbent per unit mass is at most 10 mg/g as measured by using a 1 wt % nicotinamide aqueous solution; and (XIII) the adsorption amount of 1-menthol in the gas adsorbent per unit mass is at most 50 mg/g as measured by using a 2 wt % 1-menthol aqueous solution based on a 50 wt % methanol aqueous solution.

[8] The Gas adsorbent according to the above [1] to [7], wherein the gas adsorbent is an ion exchange resin.

[9] The gas adsorbent according to the above [8], wherein the ion exchange resin is a weakly basic anion exchange resin having amino groups.

EFFECTS OF THE INVENTION

The gas adsorbent of the present invention efficiently removes noxious substances present in cigarette smoke from a high flow rate gas stream and further, is less likely to release bad odor components such as amine impurities and free noxious components such as a monocyclic aromatic compound derived from the gas adsorbent itself.

Accordingly, the gas adsorbent of the present invention is generally used for a gas filter or apparatus to remove noxious gas, particularly, useful for a cigarette filter and a gas filter of apparatus which is required to remove noxious gas in cigarette smoke such as an air cleaner or a car air conditioner.

Further, the gas adsorbent for a cigarette filter of the present invention effectively removes acidic noxious substances such as hydrogen cyanide, whereas it is less likely to adsorb flavorous components useful for a cigarette such as nicotinamide originally contained in a cigarette and 1-menthol to be added to a cigarette, and it is less likely to release bad odor components derived from the gas adsorbent itself such as amine impurities and free noxious components derived from the gas adsorbent itself such as a monocyclic aromatic compound.

Accordingly, the gas adsorbent for a cigarette filter can selectively remove noxious gas components in cigarette smoke without impairing the flavor of a cigarette.

MEANINGS OF SYMBOLS

Figure 1:
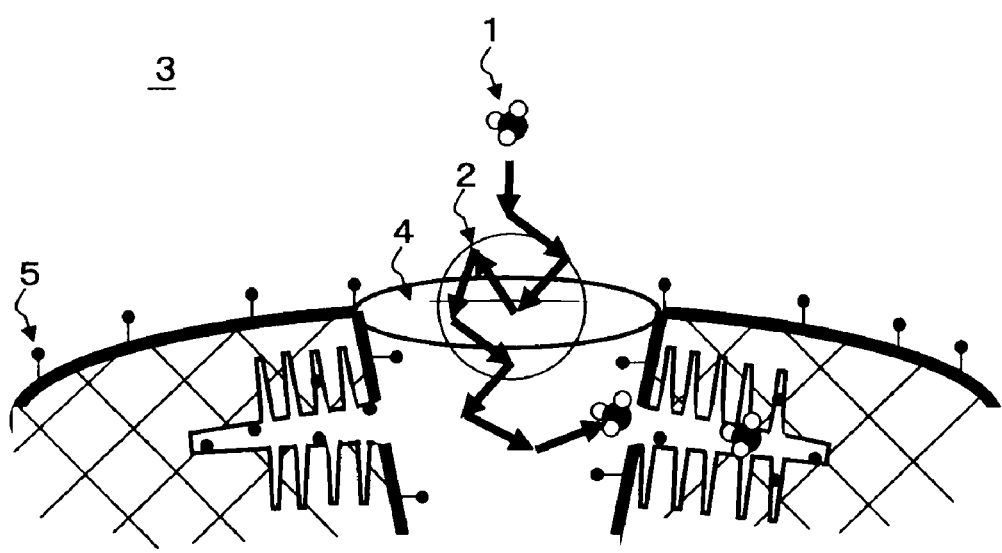
FIG. 1 is a drawing schematically illustrating the (estimated) mechanism of capturing noxious substances in a gas stream by the gas adsorbent of the present invention.

1: Noxious component molecule
2: Mean free path of noxious component molecule
3: Gas adsorbent
4: Pore size
5: Ion exchange group

BEST MODE FOR CARRYING OUT THE INVENTION

Now, the present invention will be described in detail. However, the following description is one example of the present invention, and the present invention is not limited thereto. Further, in the present invention, "µeq/g" and "meq/g" respectively represents "$10^{-3}$ mol/kg" and "mol/kg" in the SI unit system.

[1] Gas Adsorbent According to a First Aspect of the Present Invention

The gas adsorbent according to a first aspect provided by the present invention satisfies the following conditions (I), (II), (IV) and (V) or the following conditions (I), (III), (IV) and (V):

(I) the mean pore radius of the gas adsorbent is at least 330 Å and at most 3,000 Å as measured by a mercury porosimeter;

(II) the amine elution amount from the gas adsorbent per unit mass is at most 10 µeq/g;

(III) the content of a monocyclic aromatic compound represented by the following formula 1 in the gas adsorbent per unit mass is at most 4 mg/g:

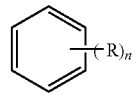

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different;

(IV) the neutral salt decomposition capacity is at most 0.43 meq/g; and (V) the acid adsorption capacity of the gas adsorbent per unit mass is at least 1.5 meq/g.

Now, the above gas adsorbent of the present invention will be described in detail.

First, among the above conditions, the condition (I) will be described.

In general, a gas adsorbent being a porous material having a large number of pores, is excellent in the gas adsorptivity such as the adsorption amount of gas and the adsorption efficiency, since the area of contact between the gas adsorbent and the gas to be treated is large. However, the adsorption efficiency of gas varies also by the pore radius of the gas adsorbent.

Among conventional gas adsorbents, for example, a porous material such as activated carbon or silica gel has a mean pore radius of from about 10 to 30 Å and Duolite A7 which is an ion exchange resin has a mean pore radius of from about 150 to about 300 Å. However, the above mean pore radius is small for the gas component to sufficiently be diffused in the pores, whereby the gas adsorption efficiency is poor, and particularly at a high gas flow rate of from about 10 to about 30 m/sec as that when gas passes through a cigarette filter during smoking (aspiration), the gas adsorptivity is low.

Accordingly, the present invention defines the mean pore radius of a gas adsorbent as an index of the gas adsorptivity so as to efficiently bringing in and adsorb aimed substances from a gas stream having a relatively high flow rate as that when gas passes through a cigarette filter during smoking.

Namely, the gas adsorbent according to a first aspect of the present invention has, as defined in the above condition (I), a mean pore radius of at least 330 Å, preferably at least 350 Å, and at most 3,000 Å, preferably at most 2,500 Å. Further, the gas adsorbents according to second to seventh aspects of the present invention have a mean pore radius of usually at least 330 Å, preferably at least 350 Å, and usually at most 10,000 Å, preferably at most 5,000 Å, furthermore preferably at most 3,000 Å, particularly preferably at most 2,500 Å. When the mean pore radius of the gas adsorbent is within the above range, not only the surface area is merely increased but also excellent bringing properties of the gas adsorbent into pores and gas diffusibility in the pores are obtained even at a high gas flow rate of from about 10 to about 30 m/sec, whereby high performance as a gas adsorbent can be exhibited.

The mean pore radius is a parameter regarding the pore structure on the resin surface and is represented by the average of radii of pores on the resin surface.

Usually, for gas adsorption, molecular sieve-like diffusion and surface diffusion such that a pore structure having a size several times the size of molecules to be captured is optimum, are considered. However, according to the studies by the present inventor, it was found that requirements of the pore radius of a resin (gas adsorbent) is a larger structure (Knudsen diffusion region). The reason is unclear, but the following mechanism is estimated.

In general, molecules of noxious components in gas move within a range of the mean free path. The mean free path is known to be about 300 Å in the case of acetaldehyde which is one of carbonyl compounds, about 200 Å in the case of acetone and about 500 Å in the case of hydrogen cyanide, for example, at 250° C. under atmospheric pressure. Accordingly, with a gas adsorbent having pore sizes of at least the mean free path, molecules of the noxious components can be guided into pores of the gas adsorbent (FIG. 1).

The mean free path is an average distance each atom or molecule travels between one collision and the next collision. It indicates how far a gas molecule carries a certain physical property when it repeatedly moves while it collides with another molecule or atom until the next collision, and it plays an important role in transportation properties such as a diffusion coefficient (Chemical Dictionary, TOKYO KAGAKU DOJIN CO., LTD., page 1289).

Accordingly, preferred is a pore structure having the above mean pore radius and in addition, having a large number of pores having pore radii of usually at least 300 Å, preferably at least 400 Å, particularly preferably at least 500 Å. Specifically, preferred is one having the above pores with a pore volume of usually at least 0.05 ml/g, preferably at least 0.1 ml/g, more preferably at least 0.3 ml/g, particularly preferably at least 0.5 ml/g.

Here, if the pore radius is too large, the surface area of the resin (gas adsorbent) tends to be small, whereby the adsorption amount of noxious components may be insufficient.

The mean pore radius can be measured by a mercury porosimeter. By the mercury porosimeter, mercury which has a large surface tension and which will not react with most substances under pressure is injected into pores of a vacuum dried sample (the gas adsorbent in the present invention), and the relation between the pressure applied and the volume of mercury infiltrated into the pores is measured.

In general, the pressure when mercury is infiltrated into pores of the gas adsorbent under pressure and the pore size into which mercury can be infiltrated under the pressure, is represented by Washburn equation of the formula (1):

$$Pr = -2\sigma \cos\theta \quad (1)$$

wherein P is the pressure, r is the pore radius, $\sigma$ is the surface tension of mercury and is usually about 480 dyne/cm, and $\theta$ is the contact angle between mercury and the wall of pores and is usually about 140°.

The mean pore radius can be calculated based on the above formula (1) from the pressure and the amount of mercury infiltrated into the pores of a sample, assuming that pores are cylindrical.

A specific example of the measuring method is shown below.

(Method of Measuring Pore Physical Properties)

A vacuum dried resin (gas adsorbent) is put in a glass cell, and the pore radius and the pore volume of the resin are measured by a mercury porosimeter. From a histogram representing the pore distribution, indicating the pore volume and the pore radius respectively by the vertical axis and the horizontal axis, the pore radius at a portion with the largest total amount of the pore volumes is regarded as the mean pore radius.

In order that the mean pore radius of the gas adsorbent is within the above range, it is preferred to use, as a base material of the gas adsorbent, a polymer resin having a three-dimensional crosslinked structure selected from an aromatic polymer resin, a (meth)acrylic polymer resin and a phenol polymer resin.

Here, the aromatic polymer resin is a polymer resin having an aromatic ring in the main chain or in the side chain of the polymer and may, for example, be a copolymer of a monovinyl aromatic monomer with a crosslinkable aromatic monomer.

The (meth)acrylic polymer resin is a polymer resin having repeating units derived from a (meth)acrylic monomer in the main chain or the side chain of the polymer, and may, for example, be a polymer of one or more (meth)acrylic monomers or a copolymer of one or more (meth) acrylic monomers with one or more vinyl monomers other than the (meth) acrylic monomer.

The phenol polymer resin is a polycondensate of one or more phenol compounds.

Further, when silica is used as the base material of the gas adsorbent, for example, the pore size can be controlled by the following method. In general, silica is obtained by blending a silicon alkoxide such as tetraethoxysilane, a solvent and water and forming them into a gel, followed by aging and drying, and the pore size can be controlled by changing precipitation conditions when formed into a gel, thermal decomposition conditions or the like. Further, it is also possible to control the pore structure by adding a surfactant containing an amine having a long alkyl chain and/or an ammonium salt when the above silicon alkoxide, solvent and water are blended and gelating them.

By controlling the alkyl chain in the surfactant, water, the solvent and the gel point, desired pores can be obtained.

Now, among the above conditions, the condition (II) will be described.

Among conventional gas adsorbents, as one having relatively favorable adsorptivity for noxious components such as carbonyl compounds, one having amino groups fixed to the base of the matrix structure, such as an ion exchange resin having amino groups as disclosed in Patent Documents 3 and 4, and a reagent having 3-aminopropylsilyl groups bonded to silica gel as disclosed in Patent Document 1, has been known.

However, a part of an amino compound used in the preparation step remains unreacted without being fixed to the base of the matrix structure, and is contained as impurities in the gas adsorbent. This unreacted amino compound may cause an amine odor or leakage of the amine compound.

In general, the larger the amount of amino groups fixed in the gas adsorbent, the more the adsorptivity for carbonyl compounds improves, but the amount of the remaining unreacted amino compound also increases. Accordingly, a conventional gas adsorbent having favorable carbonyl compound adsorptivity contains amine odor components derived from the gas adsorbent itself, which emit bad odor and thereby inhibit use as a gas adsorbent.

To solve such problems, in the gas adsorbent of the present invention, the intensity of the amine odor which is a bad odor is defined employing the amine elution amount of the gas adsorbent per unit mass as an index.

Namely, the gas adsorbent of the present invention not only satisfies the above condition (I) of the mean pore radius but also satisfies, as defined by the above condition (II), that the amine elution amount from the gas adsorbent per unit mass is at most 10 µeq/g, preferably at most 5 µeq/g, more preferably at most 1 µeq/g, particularly preferably at most 0.1 µeq/g, whereby it emits very little bad odor derived from the gas adsorbent itself, particularly an amine odor.

The amine elution amount is measured, for example, by using an organic or inorganic strongly acidic aqueous solution as follows.

(Amine Elution Test Method)

The gas adsorbent as a test specimen is packed in a column, and as an eluent, for example, a 0.5 to 5 N hydrochloric acid aqueous solution is made to flow to elute amines. The obtained eluant is measured by an analysis method capable of quantitatively determining amines such as column chromatography, liquid chromatography, mass spectrometry or nuclear magnetic resonance spectroscopy.

In order that the amine elution amount from the gas adsorbent is within the above range, the unreacted amino compound should be removed by e.g. a method of washing the gas adsorbent after introduction of amino groups with an organic solvent such as methanol, acetone, propanol or tetrahydrofuran (THF). The above washing may be carried out with heating as the case requires. Further, the washing method may be batch washing or liquid flow through the column. Washing with the above organic solvent may be carried out at the stage of a final product in addition to the above washing or by itself.

Now, among the above conditions, the condition (III) will be described.

Among conventional gas adsorbents, as one having relatively good adsorptivity for carbonyl compounds as the main noxious acidic gas components in a cigarette, an ion exchange resin having amino groups as disclosed in Patent Document 3 or 4 has been known. The ion exchange resin having amino groups comprises the base of a matrix structure formed by polymerizing a polymerizable monomer, followed by crosslinking as the case requires, and amino groups fixed to the base. In the synthesis step, a polymerizable monocyclic aromatic compound is used as the polymerizable monomer and/or a crosslinking agent.

However, a part of the polymerizable monocyclic aromatic compound used in the synthesis step remains unreacted or as an oligomer which could not grow to the matrix structure and is contained as impurities in the ion exchange resin. Accordingly, a conventional gas adsorbent having good carbonyl compound adsorptivity releases a monocyclic aromatic compound having a benzene ring such as toluene, styrene, divinylbenzene, ethylvinylbenzene, diethylbenzene or phenol, and such a monocyclic aromatic compound is a free noxious gas component derived from the gas adsorbent itself and is known to have influence over health and to cause a decrease in the gas adsorption amount and the gas adsorption rate, an odor, etc.

To solve such a problem, in the gas adsorbent of the present invention, releasability of entire aromatic compounds from the gas adsorbent, particularly releasability of a monocyclic aromatic compound having a benzene ring is defined employing the content of a monocyclic aromatic compound represented by the following formula 1 of the gas adsorbent per unit mass, as an index.

Namely, the gas adsorbent of the present invention has a content of a monocyclic aromatic compound represented by the following formula 1 in the gas adsorbent per unit mass of at most 4 mg/g, preferably at most 1 mg/g, more preferably at most 0.1 mg/g, furthermore preferably at most 0.01 mg/g, still furthermore preferably at most 0.001 mg/g, and it releases a very small amount of a noxious aromatic compound derived from the gas adsorbent itself, particularly a monocyclic aromatic compound having a benzene ring.

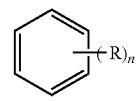

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different.

The content of the monocyclic aromatic compound represented by the formula 1 is measured, for example, as follows.

(Aromatic Compound Elution Test Method)

The gas adsorbent as a test specimen is packed in a column, and as an eluent, for example, a polar organic solvent such as isopropanol, acetone or tetrahydrofuran is made to flow to elute an aromatic compound. The obtained eluant is measured by an analysis method capable of quantitatively determining an aromatic compound such as gas chromatography, liquid chromatography, mass spectrometry or nuclear magnetic resonance spectroscopy.

In order that the content of the monocyclic aromatic compound in the gas adsorbent is within the above range, a free state monocyclic aromatic compound should be removed e.g. by a method of washing the gas adsorbent with an organic solvent such as methanol, acetone, propanol or tetrahydrofuran. The above washing may be carried out with heating as the case requires. Further, the washing method may be batch washing or liquid flow through the column. Washing with the above organic solvent may be carried out at the stage of a final product in addition to the above washing or by itself.

Now, among the above conditions, the condition (IV) will be described.

As described for the condition (II), an unreacted amine odor component in the gas adsorbent emits a bad odor and thus prevents use as a gas adsorbent.

On the other hand, the amine odor component in the gas adsorbent is also derived from a decomposed nitrogen-containing substituent (such as a quaternary ammonium group) covalently bonded to the gas adsorbent. Namely, in the present invention, by the condition (IV) as a requirement, the amount of the amine odor component caused by decomposition of the gas adsorbent is more properly defined.

The neutral salt decomposition capacity represents functional groups derived from a quaternary ammonium group among the alkali adsorption capacity or the acid adsorption capacity. As such functional groups, an OH form and a quaternary ammonium group in a dry state are known to be easily decomposed. The neutral salt decomposition capacity represents the amount of decomposition of the nitrogen-containing substituent (such as a quaternary ammonium group) chemically bonded to the gas adsorbent. Factors which accelerate decomposition of the nitrogen-containing substituent may, for example, be a counter ion being OH type (when the counter ion of the ion exchange group is OH form, the quaternary ammonium group is likely to be decomposed), heat, and dry state (the quaternary ammonium group is stabilized by hydration, but it is easily decomposed when it looses moisture).

As a result of decomposition of the nitrogen-containing substituent in the gas adsorbent, an amine odor is generated, which impairs function as a gas adsorbent. Accordingly, the neutral salt decomposition capacity can properly represents the amount of an amine odor component caused by decomposition of the nitrogen-containing substituent in the gas adsorbent.

Namely, the gas adsorbent of the present invention has, as defined by the above condition (IV), a neutral salt decomposition capacity of the gas adsorbent per unit mass of at most 0.43 meq/g, preferably at most 0.2 meq/g, more preferably at most 0.15 meq/g, particularly preferably at most 0.1 meq/g, and it emits very little bad odor derived from the gas adsorbent itself, particularly an amine odor. The lower limit of the neutral salt decomposition capacity is most preferably 0, and is usually from 0.01 to 0.05 meq/g.

The neutral salt decomposition capacity is measured, for example, as follows.

(Neutral Salt Decomposition Capacity Measuring Method)

The neutral salt decomposition capacity of the anion exchange resin of the present invention is analyzed and measured by the following method.

First, the anion exchange resin is packed in a column, and a 5% NaCl aqueous solution in an amount 25 times the capacity of the resin is made to flow to convert counter ions to Cl form. 10.0 ml of the resin is weighed, and a 2N NaOH aqueous solution is made to flow in an amount of 75 times to regenerate the Cl form to OH form. The resin is sufficiently washed with deionized water until the eluant used for washing becomes neutral, and a 5% NaCl aqueous solution is made to flow in an amount of 25 times and all the discharged liquid is collected. The discharged liquid is titrated with 1 N hydrochloric acid or 0.1 N hydrochloric acid to measure the neutral salt decomposition capacity. The value is calculated as a value per 1 ml resin, to determine the neutral salt decomposition capacity per volume. Further, 10.0 ml of the resin is measured by a measuring cylinder and drained by a centrifugal separator, and the weight of the resin after drained is measured. The resin is dried by a vacuum dryer at 50° C. for 8 hours, and the resin weight after drying is measured. The neutral salt decomposition capacity per dry weight is calculated from the weight after drained and the weight after drying.

In order than the neutral salt decomposition capacity of the gas adsorbent is within the above range, a known method to suppress the neutral salt decomposition capacity of the gas adsorbent may be employed. For example, when the gas adsorbent is silica, a method of preliminarily reacting an amine species having an amino group, such as aminopropyltrialkoxysilane or 3(2(2-aminomethylamino)ethylamino)propyl-trimethoxysilane may be mentioned. Further, when the gas adsorbent is an ion exchange resin, in a case where an amine species is reacted with a chloromethyl group in an ion exchange resin precursor, the neutral salt decomposition capacity can be reduced by use of the amine species such as dimethylamine in a large excess. Further, in a case where an amine species such as a polyethylene polyamine represented by diethylenetriamine is reacted, the neutral salt decomposition capacity can be suppressed low by reducing the amine amount.

Further, since a by-product quaternary ammonium salt is likely to be thermally decomposed, a method of reducing the neutral salt decomposition capacity by preliminary heating to decompose an ammonium group may also be used.

Now, among the above conditions, the condition (V) will be described.

(V) The acid adsorption capacity of the gas adsorbent per unit mass is at least 1.5 meq/g.

As described for the condition (I), it is estimated that a gas adsorbent having a larger pore radius than that of a conventional gas adsorbent can guide noxious components into pores of the gas adsorbent, whereby it is excellent in bringing properties into pores and gas diffusibility in the pores, and has high performance as a gas adsorbent. However, the gas adsorption efficiency varies also by whether how it can maintain the noxious components brought into the pores, i.e. the amount of adsorption of the noxious gas components in the gas adsorbent.

For example, it was found that even when the mean pore radius is so large as 330 Å or larger, if the amount of adsorption of the noxious gas components is small, the gas components can not be maintained even if they are sufficiently diffused in the pores, whereby the gas adsorption efficiency is poor, thus lowering the gas adsorptivity.

Accordingly, in the present invention, in order that the aimed substances efficiently brought are more efficiently adsorbed, the acid adsorption capacity per unit mass of the gas adsorbent is defined as the index of the gas adsorptivity. Cigarette smoke contains, as acidic noxious gas other than low molecular weight aliphatic aldehydes, organic acids such as formic acid, acetic acid and propionic acid, sulfur dioxide, nitrogen dioxide, hydrochloric acid, nicotinic acid, hydrogen cyanide, hydrogen sulfide, etc. Accordingly, such other acidic noxious gas contained in cigarette smoke are also noxious gas components which are highly likely to be present in the living environment.

Accordingly, in the present invention, it is preferred to define adsorptivity for entire acidic noxious gases of the gas adsorbent, particularly hydrogen cyanide and hydrogen sulfide contained in the cigarette smoke, employing the acid adsorption capacity of the gas adsorbent per unit mass as an index.

In the present invention, when the acid adsorption capacity of the gas adsorbent per unit mass is defined, the acid adsorption capacity is at least 1.5 meq/g, preferably at least 2.0 meq/g, more preferably at least 2.5 meq/g, particularly preferably at least 3.0 meq/g, especially preferably at least 3.5 meq/g.

A test of measuring the acid adsorption capacity is carried out, for example, by using a 0.5 to 5 N hydrochloric acid aqueous solution as a test solution as follows.

(Acid Adsorption Capacity Measuring Test Method)

A sodium hydroxide aqueous solution is brought into contact with the gas adsorbent as a test specimen to regenerate the acid component adsorption performance, and the gas adsorbent is mixed and sufficiently brought into contact with a predetermined amount of a 0.5 to 5 N hydrochloric acid aqueous solution. Then, a solution portion in the mixture is sampled, followed by acid-base titration with a basic solution at a predetermined concentration, e.g. a 0.5 to 5 N sodium hydroxide aqueous solution, to calculate the acid adsorption capacity from the amount of the hydrochloric acid aqueous solution used for acid adsorption and the amount of the basic solution consumed in the titration.

More specifically, the following process may be mentioned.

10.0 ml of the adsorbent is measured by a measuring cylinder and packed in a glass column, and 200 ml of a 2 N hydrochloric acid aqueous solution is made to flow, followed by washing with deionized water. Then, 250 ml of a 2 N sodium hydroxide aqueous solution is made to flow. Further, deionized water is made to flow until the discharged liquid becomes neutral. The obtained adsorbent is put in a 500 ml Erlenmeyer flask, and 300 ml of a 0.2 N hydrochloric acid aqueous solution is added, followed by shaking for 8 hours. After shaking, 20.0 ml of the supernatant liquid is sampled by a whole pipette, followed by titration with a 0.1 N sodium hydroxide aqueous solution, and the amount of adsorbed hydrochloric acid is calculated as the amount per volume to determine the acid adsorption capacity.

In order that the acid adsorption capacity of the gas adsorbent is within the above range, the amount of introduction of acid adsorption groups in the gas adsorbent should be adjusted by a known method. For example, in the case of an acrylic ion exchange resin, functional groups are introduced by reaction of glycidyl groups with an amine species, and accordingly glycidyl groups should be contained to a certain extent or more. Further, in the case of a phenol or styrene type, an amine is introduced by introduction of chloromethyl groups, and accordingly chloromethyl groups should be introduced in an amount of introduction of acid adsorption groups or more. Further, in the case of activated carbon, when amine impregnation is employed, e.g. (i) a method of using an amine having a low molecular weight so that it is diffused into the pore structure of activated carbon, (ii) a method of using an amine compound partially having a hydrophobic group such as a long chain aliphatic amine or benzylamine so as to increase the impregnation efficiency, may be employed.

In addition, the gas adsorbent according to the first aspect of the present invention preferably has the following property (VI) and/or (X). Further, when the gas adsorbent of the present invention is used as a gas adsorbent for a cigarette filter, it preferably has the following property (XII) and/or (XIII). (VI), (X), (XII) and (XIII) will be described in detail below.

(VI) The adsorption amount of propionaldehyde in the gas adsorbent per unit mass is at least 240 mg/g as measured by using a 2 wt % propionaldehyde aqueous solvent solution.

(X) After 100.0 ml of a propionaldehyde 100 ppm aqueous solution at 25° C. is brought into contact with 5 g of the gas adsorbent and left for 3 minutes, the concentration of the propionaldehyde aqueous solution is at most 80 ppm.

(XII) The adsorption amount of nicotinamide in the gas adsorbent per unit mass is at most 10 mg/g as measured by using a 1 wt % nicotinamide aqueous solution.

(XIII) The adsorption amount of 1-menthol in the gas adsorbent per unit mass is at most 50 mg/g as measured by using a 2 wt % 1-menthol solution based on a 50 wt % methanol aqueous solution.

[2] Gas Adsorbent According to a Second Aspect of the Present Invention.

The gas adsorbent according to a second embodiment provided by the present invention satisfies the following conditions (VI) and (VII):

(VI) the adsorption amount of propionaldehyde in the gas adsorbent per unit mass is at least 240 mg/g as measured by using a 2 wt % propionaldehyde aqueous solvent solution; and (VII) the content of a monocyclic aromatic compound represented by the following formula 1 in the gas adsorbent per unit mass is at most 5 μg/g:

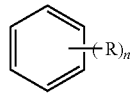

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different.

[3] Gas Adsorbent According to a Third Aspect of the Present Invention.

The gas adsorbent according to a third aspect provided by the present invention satisfies the following conditions (VIII) and (IX):

(VIII) the adsorption amount of propionaldehyde in the gas adsorbent per unit mass is at least 330 mg/g as measured by using a 2 wt % propionaldehyde aqueous solvent solution; and (IX) the amine elution amount from the gas adsorbent per unit mass is at most 10 μeq/g.

[4] The Gas Adsorbent According to a Fourth Aspect of the Present Invention

The gas adsorbent according to a fourth aspect provided by the present invention satisfies the following conditions (X) and (VII):

(X) after 100.0 ml of a propionaldehyde 100 ppm aqueous solution at 25° C. is brought into contact with 5 g of the gas adsorbent and left for 3 minutes, the concentration of the propionaldehyde aqueous solution is at most 80 ppm; and (VII) the content of a monocyclic aromatic compound represented by the following formula 1 in the gas adsorbent per unit mass is at most 5 μg/g:

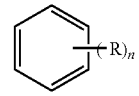

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different.

[5] Gas Adsorbent According to a Fifth Aspect of the Present Invention

The gas adsorbent according to a fifth aspect provided by the present invention satisfies the following conditions (X) and (IX):

(X) after 100.0 ml of a propionaldehyde 100 ppm aqueous solution at 25° C. is brought into contact with 5 g of the gas adsorbent and left for 3 minutes, the concentration of the propionaldehyde aqueous solution is at most 80 ppm; and (IX) the amine elution amount from the gas adsorbent per unit mass is at most 10 μeq/g.

As described above, carbonyl compounds are one of noxious gas components which are highly likely to be present in the living environment. In the present invention, the adsorptivity for entire carbonyl compounds of the gas adsorbent, particularly low molecular weight aliphatic aldehydes, preferably satisfies the above (VI), employing the adsorption amount of propionaldehyde of the gas adsorbent per unit mass as an index.

Namely, the gas adsorbent according to a second aspect of the present invention has, as defined by the above condition (VI), an adsorption amount of propionaldehyde as measured by using a 2 wt % propionaldehyde aqueous solvent solution of at least 240 mg/g, preferably at least 300 mg/g, more preferably at least 340 mg/g. Of the gas adsorbent according to a third aspect of the present invention, as defined by the above condition (VIII), the adsorption amount of propionaldehyde as measured by using a 2 wt % propionaldehyde aqueous solvent solution is at least 330 mg/g, preferably at least 340 mg/g.

The gas adsorbent of the present invention is excellent in adsorptivity for carbonyl compounds among noxious gas components, and is particularly excellent in adsorptivity for low molecular weight aliphatic aldehydes having carbon numbers of from about 1 to about 5, such as formaldehyde, acetaldehyde, propionaldehyde, butylaldehyde, crotonaldehyde and acrolein. The above "adsorptivity" and "adsorption amount" not only include an embodiment in which a carbonyl compound is practically adsorbed in the gas adsorbent but also include an embodiment in which a carbonyl compound undergoes aldol condensation to form a multimer by functional groups (e.g. anion exchange groups) contained in the gas adsorbent as a catalyst, and resultingly, a volatile carbonyl compound is reduced.

For a propionaldehyde adsorption test, an aqueous solvent solution adjusted to have a propionaldehyde concentration of 2 wt % is used as a test solution. The aqueous solvent used for preparation of the test solution is, for example, simple water such as deionized water or pure water, or a mixture of a water-soluble organic solvent with water, and is preferably simple water or a water-soluble organic solvent mixture containing at most 50 wt % of a water-soluble organic solvent. As a specific example of the test solution, a 10 wt % methanol (MeOH) aqueous solution at a propionaldehyde concentration of 2.0 wt % may be used.

A propionaldehyde adsorption test is carried out, for example, as follows.

(Propionaldehyde Adsorption Test Method)

The gas adsorbent as a test specimen is mixed with the propionaldehyde aqueous solvent solution adjusted to have the above predetermined concentration, followed by sufficient shaking at room temperature, the supernatant liquid is sampled, and the concentration of propionaldehyde is measured by an analysis method capable of quantitatively determining propionaldehyde such as gas chromatography, liquid chromatography, mass spectrometry or nuclear magnetic resonance spectroscopy to calculate the adsorption amount.

In order that the adsorption amount of propionaldehyde in the gas adsorbent is within the above range, it is properly adjusted by increasing the pore radius of the gas adsorbent as described above and in addition, by increasing the acid adsorption capacity.

Here, under such circumstances that the present invention is to adsorb "gas", in order to more properly describe the gas adsorbent of the present invention from the viewpoint of the adsorption rate, the adsorptivity for a carbonyl compound is defined by the decrement of the propionaldehyde concentration measured by the following method.

Namely, of the gas adsorbent according to a fourth or fifth aspect of the present invention, as defined by the above condition (X), after 100.0 ml of a propionaldehyde 100 ppm aqueous solution at 25° C. is brought into contact with 5 g of the gas adsorbent and left for 3 minutes, the concentration of the propionaldehyde aqueous solution is at most 80 ppm. The propionaldehyde concentration after 3 minutes is more preferably at most 70 ppm. Further, the propionaldehyde concentration after 10 minutes is usually at most 60 ppm, preferably at most 50 ppm, more preferably at most 45 ppm.

The above propionaldehyde adsorption rate test is carried out, for example, as follows.

(Propionaldehyde Adsorption Rate Test Method)

5.0 g of the gas adsorbent (as drained in the case of an ion exchange resin) is added to a 300 ml Erlenmeyer flask, and 100.0 ml of a propionaldehyde aqueous solution at a concentration of 100 ppm preliminarily adjusted to a temperature of 25° C. is instantaneously injected thereto. The flask is shaken by a shaker set at 25° C. under conditions under which the resin is maintained in a suspended state, and three minutes and ten minutes after charge of the propionaldehyde aqueous solution, the supernatant liquid is sampled to calculate the concentration of propionaldehyde by high performance liquid chromatography (HPLC) and/or gas chromatography (GC).

In order that the adsorption rate of propionaldehyde into the gas adsorbent is within the above range, it is properly adjusted by increasing the pore radius of the gas adsorbent as described above and in addition, by increasing the acid adsorption capacity.

Some consider that the results of the propionaldehyde adsorption rate test method for the condition (X) do not properly represent a phenomenon of capturing noxious substance gas originally in the gas phase system, in that an aqueous solution is brought into contact with the gas adsorbent. However, as shown in the after-mentioned Examples, the adsorption amount represented by the propionaldehyde adsorption rate test method for the condition (X) is substantially in proportion to the gas adsorption amount as a result of the following gas phase system gas capture test. Accordingly, it is considered that the condition (X) substantially properly represents the gas capturing performance in the gas phase system.

As described above, when the gas adsorbent of the present invention satisfies any of the above (VI), (VIII) and (X), it has high adsorptivity for noxious substance carbonyl compounds.

On the other hand, such a condition is required that release of bad odor components derived from the gas adsorbent itself such as a monocyclic aromatic compound and amine impurities is small.

Accordingly, the gas adsorbents according to second and fourth aspects of the present invention are required to satisfy the following condition (VII):

(VII) the content of a monocyclic aromatic compound represented by the following formula 1 in the gas adsorbent per unit mass is at most 5 μg/g:

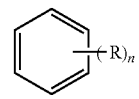

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different.

The content of the monocyclic aromatic compound represented by the above formula 1 in the gas adsorbent per unit mass is preferably at most 1 μg/g, more preferably at most 0.8 μg/g.

When the content of the monocyclic aromatic compound is within the above range, the amount of release of a noxious aromatic compound derived from the gas adsorbent itself, particularly a monocyclic aromatic compound having a benzene ring, is very small.

The content of the monocyclic aromatic compound represented by the above formula 1 is measured, for example, in the same manner as in the above-described (aromatic compound elution test method).

Further, the gas adsorbents according to third and fifth aspects of the present invention are required to satisfy the following condition (IX):

(IX) the amine elution amount from the gas adsorbent per unit mass is at most 10 μeq/g.

The amine elution amount from the gas adsorbent per unit mass is preferably at most 5 μeq/g, more preferably at most 1 μeq/g, especially preferably at most 0.1 μeq/g. When the amine elution amount is within the above range, a bad odor derived from the gas adsorbent itself particularly an amine odor is very little.

The amine elution amount is measured, for example, in the same manner as in the above-described (amine elution test method).

[6] Gas Adsorbent According to a Sixth Aspect of the Present Invention

The gas adsorbent according to a sixth aspect provided by the present invention satisfies the following conditions (XI) and (XII) and/or the following conditions (XI) and (XIII) and is used as a component of forming a cigarette filter:

(XI) the amine elution amount from the gas adsorbent per unit mass is at most 10 μeq/g, and the adsorption amount of an acidic component in the gas adsorbent per unit mass is at least 2.5 meq/g;

(XII) the adsorption amount of nicotinamide in the gas adsorbent per unit mass is at most 10 mg/g as measured by using a 1 wt % nicotinamide aqueous solution; and (XIII) the adsorption amount of 1-menthol in the gas adsorbent per unit mass is at most 50 mg/g as measured by using a 2 wt % 1-menthol solution based on a 50 wt % methanol aqueous solution.

[7] Gas Adsorbent According to a Seventh Aspect of the Present Invention

The gas adsorbent according to a seventh aspect provided by the present invention satisfies the following conditions (XIV) and (XII) and/or the following conditions (XIV) and (XIII) and is used as a component of forming a cigarette filter.

(XIV) the content of a monocyclic aromatic compound represented by the following formula 1 in the gas adsorbent per unit mass is at most 10 μg/g, and the adsorption amount of an acidic component in the gas adsorbent per unit mass is at least 2.5 meq/g:

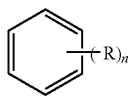

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different;

(XII) the adsorption amount of nicotinamide in the gas adsorbent per unit mass is at most 10 mg/g as measured by using a 1 wt % nicotinamide aqueous solution; and (XIII) the adsorption amount of 1-menthol in the gas adsorbent per unit mass is at most 50 mg/g as measured by using a 2 wt % 1-menthol solution based on a 50 wt % methanol aqueous solution.

Nicotinamide is one of flavorous components originally contained in cigarette smoke and imparts cigarette's flavor. Accordingly, when the gas adsorbent of the present invention is used for a cigarette filter, it is preferred to define the adsorptivity of the gas adsorbent for entire gas components which impart cigarette's flavor particularly nicotinamide contained in cigarette smoke, employing the adsorption amount of nicotinamide in the gas adsorbent per unit mass as an index.

Namely, with respect to the gas adsorbents according to sixth and seventh aspects of the present invention, the adsorption amount of nicotiamide in the gas adsorbent per unit mass as measured by using a 1 wt % nicotinamide aqueous solution is at most 10 mg/g, preferably at most 1 mg/g, more preferably at most 0.1 mg/g. When the adsorption amount of nicotinamide in the gas adsorbent is within the above range, flavorous components characteristic of a cigarette will not be impaired.

The adsorption amount of nicotinamide represented by the following formula 2 is measured, for example, by using a 1 wt % nicotinamide aqueous solution as a test solution as follows:

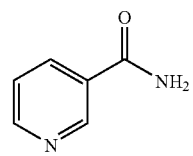

(Nicotinamide Adsorption Test Method)

First, as a test solution, a nicotinamide aqueous solution adjusted to have the above predetermined concentration is prepared. Then, the gas adsorbent as a test specimen is mixed with the test solution, followed by sufficient shaking at room temperature, the supernatant liquid is sampled, and the concentration of nicotinamide is measured by an analysis method capable of quantitatively determining nicotinamide such as gas chromatography, liquid chromatography, mass spectrometry or nuclear magnetic resonance spectroscopy to calculate the adsorption amount.

In order that the adsorption amount of nicotinamide in the gas adsorbent is within the above range, hydrophilic groups (ion exchange groups) should be introduced to the gas adsorbent in a large amount. Namely, as described above, it is properly adjusted by increasing the acid adsorption amount.

1-Menthol is one of flavorous components mainly added to a cigarette and imparts pleasant cooling sensation. Accordingly, when the gas adsorbent of the present invention is used for a cigarette filter, it is preferred to define the adsorptivity of the gas adsorbent for entire gas components to impart pleasant cooling sensation particularly 1-menthol to be added to a cigarette, employing the adsorption amount of 1-menthol in the gas adsorbent per unit mass as an index.

Namely, with respect to the gas adsorbents according to sixth and seventh aspects of the present invention, the adsorption amount of 1-menthol in the gas adsorbent per unit mass is at most 50 mg/g, preferably at most 40 mg/g, more preferably at most 30 mg/g. When the adsorption amount of 1-menthol in the gas adsorbent is within the above range, flavorous components added to a cigarette will not be impaired.

In 1-menthol adsorption test, 1-menthol represented by the following formula 3 is subjected to tests in the form of a 2 wt % 1-menthol aqueous solution based on a 50 wt % methanol aqueous solution.

1-Menthol adsorption test is carried out, for example, as follows.

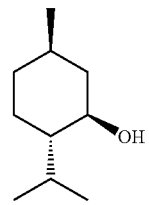

(1-Menthol Adsorption Test Method)

The gas adsorbent as a test specimen is mixed with a 2 wt % 1-menthol solution based on a 50 wt % methanol aqueous solution adjusted to have the above predetermined concentration, followed by sufficient shaking at room temperature, the supernatant liquid is sampled, and the concentration of 1-menthol is measured by an analysis method capable of quantitatively determining 1-menthol such as gas chromatography, liquid chromatography, mass spectrometry or nuclear magnetic resonance spectroscopy to calculate the adsorption amount.

In order that the adsorption amount of 1-menthol in the gas adsorbent is within the above range, hydrophilic groups (ion exchange groups) should be introduced in a large amount to the gas adsorbent. Namely, as described above, it is properly adjusted by increasing the acid adsorption amount.

When the gas adsorbent of the present invention satisfies the above condition (XII) and/or (XIII), it is less likely to adsorb flavorous components useful for a cigarette such as nicotinamide originally contained in a cigarette and 1-menthol to be added to a cigarette.

In addition, such a condition is required that acidic noxious substances such as hydrogen cyanide are effectively removed and in addition, release of bad odor components derived from the gas adsorbent itself such as amine impurities is small.

Accordingly, the gas adsorbent according to a sixth aspect of the present invention is required to satisfy the following condition (XI):

(XI) the amine elution amount from the gas adsorbent per unit mass is at most 10 µeq/g, and the adsorption amount of an acidic component in the gas adsorbent per unit mass is at least 2.5 meq/g.

Further, the gas adsorbent according to a seventh aspect of the present invention is required to satisfy the following condition (XIV):

(XIV) the content of a monocyclic aromatic compound represented by the following formula 1 in the gas adsorbent per unit mass is at most 10 µg/g, and the adsorption amount of an acidic component in the gas adsorbent per unit mass is at least 2.5 meq/g:

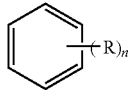

wherein R is a substituent selected from the group consisting of a hydroxyl group, a $C_{1-3}$ alkyl group and a $C_{2-3}$ alkenyl group, and n is an integer of from 1 to 6 and represents the number of the substituent R, provided that when there are a plurality of R's, the respective R's may be the same or different.

The amine elution amount from the gas adsorbent per unit mass is preferably at most 5 µeq/g, more preferably at most 1 µeq/g, especially preferably at most 0.1 µeq/g. When the amine elution amount is within the above range, a bad odor derived from the gas adsorbent itself particularly an amine odor is very little.

The amine elution amount is measured, for example, in the same manner as in the above-described (amine elution test method).

The content of the monocyclic aromatic compound represented by the above formula 1 in the gas adsorbent per unit mass is preferably at most 5 µg/g, more preferably at most 1 µg/g.

When the content of the monocyclic aromatic compound is within the above range, the amount of release of noxious aromatic compounds derived from the gas adsorbent itself particularly a monocyclic aromatic compound having a benzene ring is very small.

The content of the monocyclic aromatic compound represented by the formula 1 is measured, for example, in the same manner as in the above-described (aromatic compound elution test method).

The adsorption amount of an acidic component is preferably at least 3 meq/g, more preferably at least 4 meq/g, particularly preferably at least 4.5 meq/g.

The acidic component adsorption amount is measured, for example, in the same manner as in the above-described (acidic component adsorption test method).

As described above, the gas adsorbent according to a sixth aspect of the present invention which satisfies the above conditions (XI) and (XII) and/or the conditions (XI) and (XIII), and the gas adsorbent according to a seventh aspect of the present invention which satisfies the above conditions (XIV) and (XII) and/or the following conditions (XIV) and (XIII), can selectively remove noxious gas components in cigarette smoke without impairing the flavor of a cigarette.

In addition, the gas adsorbent of the present invention may have the following properties.

For application to removal of noxious gas such as a cigarette filter, an air cleaner or a car air conditioner, the transit rate of the noxious gas through the gas adsorbent is very high. Considering such a point, the number average particle size of the gas adsorbent of the present invention is preferably usually at least 50 µm, more preferably at least 100 µm, particularly preferably at least 300 µm, and preferably usually at most 1,500 µm, more preferably at most 800 µm, particularly preferably at most 750 µm, especially preferably at most 600 µm. If the number average particle size of the gas adsorbent is too large, problems such as a decrease in the adsorption rate, and powdering or generation of impalpable powder due to breaking of the resin may arise. On the other hand, if the number average particle size is too small, such problems as generation of airflow resistance, deterioration of workability at the time of packing in a filter, flying of powder, production cost, and decrease of workability due to generation of static electricity may arise. The number average particle size of the gas adsorbent of the present invention means the number average particle size at 25° C. under a relative humidity of 50%. This is because the particle size is preferably defined by the particle size at the time of use during which moisture is maintained, and for example, in the case of an ion exchange resin, the moisture retention varies depending upon the type of ion exchange groups, the exchange capacity, etc., but is usually from 5 wt % to 30 wt % at 25° C. under a relative humidity of 50%.

The number average particle size is measured, for example, as follows.

(Number Average Particle Size Measuring Method)

Sieves with a screen mesh of 1,180 µm, 850 µm, 710 µm, 600 µm, 425 µm and 300 µm are overlaid so that the screen mesh size is smallest at the bottom. The overlaid sieves are placed on a vat, and about 100 mL of the gas adsorbent is put in the sieve of 1,180 µm on top of the pile.

Water is slowly poured on the resin from a rubber tube connected to water works to remove small particles downward by sieving. From the gas adsorbent remaining in the sieve of 1,180 µm, small particles are further removed by sieving strictly by the following method. Namely, another vat is filled with water to about half the depth, and the sieve of 1,180 μm is repeatedly shaken by imparting up-and-down and rotational motions in the vat to remove small particles by sieving.

The small particles in the vat are recovered to the second largest sieve of 850 μm, and the gas adsorbent remaining on the sieve of 1,180 μm is collected in another vat. If the screen mesh is clogged with the gas adsorbent, the sieve is put on a vat upside down, a rubber tube connected to water works is closely contacted, and the gas adsorbent in the screen mesh is taken out by fast running water. The taken out gas adsorbent is transferred to the vat in which the gas adsorbent remaining on the sieve of 1,180 μm is collected, and the total volume is measured by a measuring cylinder, which is regarded as "a" (mL). The anion exchange resin which passed through the sieve of 1,180 μm is subjected to the same operation regarding the sieves of 850 μm, 710 μm, 600 μm, 425 μm and 300 μm, volumes b (mL), c (mL), d (mL), e (mL) and f (mL) are obtained by using a measuring cylinder, and finally, the volume of the resin which passed through the sieve of 300 μm is measured by a measuring cylinder and regarded as g (mL).

Assuming $V=a+b+c+d+e+f+g$, $a/V \times 100 = a'(\%)$ $b/\times 100 = b'(\%)$, $c/\times 100 = c'(\%)$, $d/\times 100 = d'(\%)$ $e/\times 100 = e'(\%)$, $f/\times 100 = f'(\%)$ and $g/\times 100 = g'(\%)$ are calculated.

From the above a' to g', the sum total (%) of the residue on the respective sieves is plotted on one axis and the size (mm) of the screen mesh is plotted on the other axis, which are plotted on logarithmic probability paper. Three points of first to third largest residue are taken, and a line which satisfies these three points as far as possible is drawn, from which the size (mm) of the screen mesh corresponding to a sum total of the residue of 50% is determined, which is regarded as the number average particle size.

The above method of calculating the number average particle size is a known calculation method, for example, as disclosed in "DIAION I, basic", published by Mitsubishi Chemical Corporation, Separation Materials Department, fourteenth edition (Sep. 1, 1999), pages 139 to 141.

The gas adsorbent of the present invention having the above number average particle size can be obtained by a known classification method. The classification method may, for example, be classification by a sieve, water sieving by means of water stream, or wind sieving by means of air stream.

For the gas adsorbent of the present invention, as described above, its pore structure and accompanying various properties are important factors in view of mechanism of gas adsorption. Accordingly, a material which satisfies the above various conditions can be used as the gas adsorbent of the present invention regardless of the type of the material. As a main material, a synthetic adsorbing material including an anion exchange resin or a cation exchange resin, or an adsorbent comprising an inorganic material such as silica, alumina or activated carbon as the base may be mentioned. The following may be mentioned as a method of adjusting various properties. For example, an organic or inorganic base material having the mean pore radius, the neutral salt decomposition capacity and the acid adsorption capacity as defined by the present invention is prepared, and functional groups which adsorb noxious components are introduced to the base material, followed by proper cleaning treatment to adjust the amine elution amount and the content of a monocyclic aromatic compound thereby to obtain the gas adsorbent of the present invention.

Further, by a specific preparation method as mentioned hereinafter, an organic or inorganic base material having the mean pore radius, the neutral salt decomposition capacity and the acid adsorption capacity is prepared while adjusting the amine elution amount or the content of a monocyclic aromatic compound as defined by the present invention, thereby to obtain the gas adsorbent of the present invention. In such a case, no cleaning treatment after introduction of functional groups is required in some cases, but cleaning treatment is preferably carried out.

Otherwise, properties of an existing ion exchange resin (synthetic adsorbent) such as an anion exchange resin or a cation exchange resin or an existing adsorbent comprising an inorganic material such as silica, alumina or activated carbon as the base, are adjusted by e.g. cleaning treatment to obtain the gas adsorbent of the present invention.

Here, the base material may differ in physical properties from a final product in some cases due to shrinkage or swelling under conditions of cleaning and post-treatment. Accordingly, in a case where an organic or inorganic base material is prepared or when an existing synthetic adsorbent is used as the base material, it is required to design the base material so that the "final product" has the mean pore radius, the neutral salt decomposition capacity and the acid adsorption capacity as defined by the present invention.

Specifically, for example, the following adjustment is required.
(i) The base polymer is designed to have a mean pore radius slightly larger than the expected mean pore radius of the final product.
(ii) The base polymer is designed to have an acid adsorption capacity larger than the expected acid adsorption capacity of the final product.

The synthetic adsorbent is a synthetic resin comprising a matrix having a three-dimensionally crosslinked polymer structure and functional groups having ion exchange capacity chemically, physically or physicochemically fixed to the matrix, and it may, for example, be an aromatic synthetic adsorbent, a (meth)acrylic synthetic adsorbent (in the present invention, "(meth)acrylic" means "acrylic" and/or "methacrylic") or a phenol synthetic adsorbent.

The aromatic synthetic adsorbent may be a synthetic adsorbent having a crosslinked structure skeleton obtained by copolymerizing a monovinyl aromatic monomer and a crosslinkable aromatic monomer. The monovinyl aromatic monomer may be an alkyl-substituted styrene such as styrene, methylstyrene or ethylstyrene, or a halogen-substituted styrene such as bromostyrene. Among them, styrene or a monomer comprising styrene as the main body is preferred. Further, the crosslinkable aromatic monomer may, for example, be divinylbenzene, trivinylbenzene, divinyltoluene, divinylnaphthalene or divinylxylene. Among them, preferred is divinylbenzene. Industrially produced divinylbenzene usually contains ethylvinylbenzene (ethylstyrene) as a by-product in a large amount, and in the present invention, such divinylbenzene may also be used. Specifically, for example, a styrene/divinylbenzene synthetic adsorbent may be mentioned.

The (meth)acrylic synthetic adsorbent may be a matrix comprising a crosslinking agent moiety containing a poly (meth)acrylic ester of a polyhydric alcohol and a basic skeleton moiety containing an ester and/or ether having a polymerizable unsaturated group and a functional group.

The poly(meth)acrylic ester of a polyhydric alcohol may, for example, be ethylene glycol di(meth)acrylate, diethylene glycol di(meth)acrylate, propylene glycol di(meth)acrylate, glycerol poly(meth)acrylate, polyethylene glycol (meth) acrylate, trimethylolpropane tri(meth)acrylate, pentaerythritol tetra(meth)acrylate or 1,3-butylene glycol di(meth)acrylate. Among them, ethylene glycol di(meth)acrylate is preferred.

The ester and/or ether having a polymerizable unsaturated group and a functional group may, for example, be a glycidyl ester of a carboxylic acid (preferably having from 3 to 12 carbon atoms) having one polymerizable vinyl group or isopropenyl group, a hydroxyalkyl ester of the above carboxylic acid, or a glycidyl ether of an alkenyl (preferably having from 3 to 12 carbon atoms) having one polymerizable vinyl group or isopropenyl group. Among them, preferred is glycidyl (meth)acrylate, allyl glycidyl ether or 2-hydroxyethyl (meth)acrylate.

Specifically, for example, a matrix comprising a methacrylic crosslinked polymer obtained by polymerizing ethylene glycol dimethacrylate, glycidyl methacrylate and divinylbenzene as a resin skeleton may be mentioned.

The phenol synthetic adsorbent may be a synthetic adsorbent obtained by polycondensing a phenol compound. The phenol compound may, for example, be phenol, a phenol derivative or paraphenylenediamine.

Specifically, a phenol/formaldehyde resin may, for example, be mentioned. The phenol synthetic adsorbent may be produced, for example, by mixing catechol, phenol, paraformaldehyde and a diluted solvent in an aqueous hydrochloric acid solution, followed by polycondensation by suspension polymerization in a reversed phase.

The above synthetic adsorbent is preferably an ion exchange resin having functional groups, more preferably a weakly basic to strongly basic anion exchange resin, particularly preferably a weakly basic anion exchange rein.

Here, the "weakly basic anion exchange resin" is a resin having weakly basic anion exchange groups such as primary to tertiary amino groups. The weakly basic anion exchange resin is usually capable of anion exchange only in an acidic to neutral solution, and a strong acid such as HCl or $H_2SO_4$ or a salt of a weak base such as $NH_4Cl$ can easily be anion-exchanged, but a weak acid is hardly anion-exchanged.

On the other hand, the "strongly basic anion exchange resin" is a resin having strongly basic anion exchange groups such as quaternary ammonium groups. The strongly basic anion exchange resin is usually capable of anion exchange in a solution in the entire pH region of from acidic to alkaline, and not only a strong acid and a normal salt but also a weak acid can be anion-exchanged.

In the present invention, among the anion exchange resins, particularly a weakly basic anion exchange resin is preferred.

A preferred weakly basic anion exchange resin may be a known weakly basic anion exchange resin washed with an acid, or a crosslinked polystyrene obtained by high temperature polymerization reaction having ion exchange groups introduced.

(Weakly Basic Anion Exchange Resin Obtained by Washing with Acid)

As a known weakly basic anion exchange resin to be washed, for example, the following anion exchange resins may be mentioned.

DIAION CR20 (tradename, manufactured by Mitsubishi Chemical Corporation), WA21 (tradename, manufactured by Mitsubishi Chemical Corporation), WA30 (tradename, manufactured by Mitsubishi Chemical Corporation), HPA25 (tradename, manufactured by Mitsubishi Chemical Corporation), Duolite A361 (tradename, manufactured by Rohm & Haas), Purolite A103 (tradename, manufactured by Purolite), Amberlite IRA93 (tradename, manufactured by Rohm & Haas), Duolite A378 (tradename, manufactured by Rohm & Haas), Lewatit MP64 (tradename, manufactured by LANXESS), Dowex MWA1 (tradename, manufactured by The Dow Chemical Company) and Amberlite IRA904 (tradename, manufactured by Rohm & Haas).

The acid to be used for washing is preferably a strong acid, and it may, for example, be 0.1 to 5 N hydrochloric acid, sulfuric acid, phosphoric acid, acetic acid or nitric acid. Further, the above strong acid may be mixed with a water-soluble organic solvent, and such a water-soluble organic solvent may specifically, for example, be an alcohol such as methanol, ethanol or isopropyl alcohol, tetrahydrofuran, dioxane or dimethylformamide.

The washing is carried out by stirring the ion exchange resin in the strong acid. The liquid temperature of the acid is preferably high, whereby the washing effect is high, and it is from room temperature to 120° C., preferably from 40 to 100° C., more preferably from 40 to 80° C. The washing method may be batch washing or column washing.

A specific method of washing the weakly basic anion exchange resin will be described below.

Namely, a known weakly basic anion exchange resin is sufficiently stirred and washed by using a strong acid such as hydrochloric acid or sulfuric acid at a concentration of from 0.1 to 5 N at a temperature of from 40 to 80° C. After washing, the above resin is packed in a column, the above strong acid at a concentration of from 0.1 to 5 N at a temperature of from 40 to 80° C. is made to flow through the column, and then deionized water is made to flow to remove the excess strong acid.

Then, through the resin in the column, from 2 BV to 4 BV ("BV" means the volume (L) per 1 L of the resin (gas adsorbent)) of methanol is made to flow and further, an aqueous sodium hydroxide solution at a concentration of from 0.1 to 3 N at from room temperature to 50° C. is made to flow to convert ion exchange groups of the resin in the column to OH form. Finally, deionized water is made to flow to obtain a weakly basic anion exchange resin which satisfies conditions required in the present invention.

(Weakly Basic Anion Exchange Resin Obtained by Introducing Ion Exchange Groups to Crosslinked Polystyrene Obtained by High Temperature Polymerization Reaction)

The weakly basic anion exchange resin obtained by introducing ion exchange groups to a crosslinked polystyrene obtained by high temperature polymerization reaction may be a weakly basic anion exchange resin comprising as the base a crosslinked polystyrene obtained by polymerization at a temperature higher than the conventional reaction temperature in polymerization for the crosslinked polystyrene. By polymerization at a temperature higher than usual, remaining of impurities such as low polymer components and free polymer components derived from the base resin and formation of decomposed products can be suppressed, whereby a weakly basic anion exchange resin which satisfies conditions required in the present invention can be obtained.

High temperature polymerization may be polymerization reaction of which at least part is carried out at a high temperature of usually at least 100° C. Preferred conditions of high temperature polymerization will be described below.

(Conditions of High Temperature Polymerization Reaction)

High temperature polymerization reaction has the following technical significance. Namely, it is considered that by high temperature conditions, the above impurities such as low polymer components and free polymer components are likely to be involved in the polymerization reaction in a glass transition state or a state close thereto, whereby the amount of the remaining low polymer components and free polymer components is reduced. Further, it is considered that the structure of a polymer chain formed by polymerization will be faster and denser, whereby the remaining low polymer components and free polymer components are blocked in the polymer chain structure, and the possibility of their elution is reduced. The glass transition point of a polystyrene is usually about 105° C. at a degree of crosslinking of 105° C. and usually about 108° C. at a degree of crosslinking of 10%. Accordingly, from such a viewpoint, the polymerization temperature is usually at least 100° C., preferably at least 110° C., more preferably at least 115° C., particularly preferably at least 120° C. However, if the temperature is too high, it will take long to raise the temperature of the polymerization solution, the range of choice for the polymerization initiator may be narrowed, the production equipment tends to be expensive, the effect of reducing elution will no more be improved even if the polymerization temperature is increased, or the formed polymer may deform or decompose. Therefore, the upper limit of the temperature is usually at most 160° C., preferably at most 150° C., more preferably at most 140° C.

The time for the high temperature polymerization reaction (the time over which the temperature is 100° C. or above) is usually at least 1 hour, preferably at least 2 hours, and usually at most 20 hours, preferably at most 10 hours, more preferably at most 6 hours. If the time for the high temperature polymerization reaction is too short, no sufficient above-described effects will be obtained and on the other hand, if it is too long, the remaining polymerization initiator is small as compared with the amount required for the reaction, whereby the above-described effects may not sufficiently be obtained, or the formed polymer may deform or decompose.

The high temperature polymerization reaction may be carried out continuously, or may be carried out intermittently dividedly with periods in which the temperature is 100° C. or below. In such a case, the time over which the temperature is 100° C. or above should be within the above range in total. However, with a view to sufficiently obtaining the above-described effects, it is preferred to carry out the high temperature polymerization reaction continuously.

(Method of Polymerization Reaction)

The method of the polymerization reaction is not particularly limited, and any of various known methods such as emulsion polymerization, suspension polymerization, bulk polymerization and solution polymerization may be employed alone or in combination of two or more. The polymerization method is properly selected depending upon the type of the polymer to be obtained and the purpose of its use.

Particularly when the obtained polymer is used as an ion exchange resin or a synthetic adsorbent as described hereinafter, the polymer preferably has a granular shape particularly a spherical or substantially spherical shape, and to produce such a granular (spherical or substantially spherical) polymer, it is effective to carry out water-in-oil or oil-in-water suspension polymerization.

In the case of conducting water-in-oil or oil-in-water suspension polymerization, an aqueous phase and an oil phase are put in a reactor, and they are formed in a suspended state by a means such as stirring to carry out polymerization reaction. The dispersed phase and the continuous phase are preferably such that the ratio of (volume of the dispersed phase): (volume of the continuous phase) is usually at least 1:1, preferably at least 1:1.5, and usually at most 1:10, preferably at most 1:6, more preferably at most 1:4.

As a component of the aqueous phase, usually water is used. On the other hand, the oil phase is mainly constituted by a raw material monomer and an organic solvent used as the case requires. Further, the polymerization initiator is present in the oil phase in the case of a water-insoluble polymerization initiator such as a peroxide such as benzoyl peroxide or an azo compound such as azobisisobutyronitrile, and present in the aqueous phase in the case of a water soluble polymerization initiator such as a persulfate, hydrogen peroxide or a hydroperoxide.

Various physical properties (e.g. viscosity, specific gravity and interfacial tension) of the oil phase greatly vary depending upon the structure and the composition. Accordingly, it is preferred to adjust the specific gravity of the oil phase to be usually at least 0.8 and at most 1.4, and it is preferred to adjust the viscosity of the oil phase to be usually at least 0.1 cps (centipoise) and at most 200 cps. Further, in a case where droplets of the oil phase are suspended in the aqueous phase, the difference between the specific gravity of the aqueous phase and the specific gravity of the oil phase {(the specific gravity of the aqueous phase)−(the specific gravity of the oil phase)} is usually at least 0 and at most 0.5, preferably at most 0.2.

In a case where the aqueous phase is the continuous phase, the aqueous phase is required not to be miscible with the oil phase comprising the raw material monomer and the like, and to be an inert liquid suitable to disperse the oil phase as droplets therein. Usually, the aqueous phase contains a suspension agent. The suspension agent usable in a conventional method depends on the type, the composition and the amount of the aqueous phase components to be used. The suspension agent used here is not particularly limited and can be properly selected from suspension agents to be used for conventional suspension polymerization. As a representative example, gelatin, polyvinyl alcohol, starch, polyacrylamide, poly(dimethyldiallyl)ammonium chloride, an inorganic compound inert to water (e.g. magnesium silicate), or a cellulose ether (e.g. carboxymethyl/methyl cellulose, ethyl cellulose or hydroxypropyl cellulose) may be mentioned. Such suspension agents may be used alone or in an optional combination of two or more. However, in order to maintain uniformity of the particle size of the formed oil phase droplets without cohesion nor breaking, the type of the aqueous phase components and the concentration of the suspension agent are determined by correlation with physical properties of the oil phase. To maintain the uniformity of the particle size of the oil phase droplets, the amount of the suspension agent is usually at least 0.01 wt %, preferably at least 0.05 wt %, and usually at most 5 wt %, preferably at most 1.5 wt %, based on the total weight of the aqueous phase.

(Polymerization Atmosphere)

In the present invention, it is preferred that the amount of oxygen in the polymerization reaction system is as little as possible such that the proportion to the entire raw material monomers is usually at most 5 ppm, particularly at most 3 ppm, especially at most 1 ppm. A polymerization method while making nitrogen containing oxygen gas flow has been proposed in e.g. U.S. Pat. No. 4,192,921 or JP-A-53-124184. However, if oxygen is present in the reaction system in the polymerization reaction (particularly radical polymerization reaction), since terminal radials are likely to be copolymerized with oxygen, oxygen is involved in the polymerization reaction of the raw material monomer, whereby a polymer containing a peroxide linkage forms. As a result, the peroxide linkage will chemically and thermally cleave in a resin preparation step or washing step or during use of the resin, thus causing formation and elution of an oligomer, or the peroxide linkage is decomposed to form and cause elution of a decomposed product such as formaldehyde or benzaldehyde. Accordingly, in order to suppress elution of such an oligomer or a decomposed product, it is important to suppress the amount of oxygen in the polymerization reaction system to be very low and to maintain such a state.

In order to reduce the amount of oxygen in the reaction system, it is preferred to sufficiently replace the gaseous phase in the reactor with an inert gas and then to carry out reaction. As the deaeration method, replacement is possible with a commonly known method such as a method of bubbling an inert gas, a method of repeatedly carrying out deaeration under reduced pressure, or a method of replacing dissolved oxygen in the liquid phase or the gaseous phase with an inert gas by pressurizing and/or heating. The inert gas may, for example, be nitrogen gas or argon gas, and is preferably nitrogen gas.

(Number of Stages of Polymerization)

As described above, at least part of the polymerization reaction is required to be carried out at high temperature of 100° C. or above, and the high temperature polymerization reaction may be carried out dividedly in a plurality of stages in combination with polymerization reaction at a lower temperature.

For example, as described above, in a case where no organic solvent is present in the reaction system (for example, production of a gel form polymer), if the temperature is so high as 100° C. or above at a stage of low conversion rate of the raw material monomer, the raw material monomer together with water forms a vapor which fills the reactor, and a part thereof undergoes polymerization at the lid of the reactor and adheres as an aggregate. Accordingly, it is preferred to carry out polymerization reaction at a relatively low temperature less than 100° C. (hereinafter sometimes referred to as "former polymerization") to increase the monomer conversion rate to a certain extent and in such a case, to carry out high temperature polymerization reaction at 100° C. or above (hereinafter sometimes referred to as "latter polymerization").

In such a case, the temperature at the former polymerization is usually at least 50° C., preferably at least 60° C., more preferably at least 70° C. and usually at most 100° C., preferably at most 90° C., more preferably at most 85° C. If the temperature at the former polymerization is too low, the conversion rate of the polymerizable monomer tends to be low, and the amount of the deposit at the time of the latter polymerization tends to increase. Further, if the temperature at the former polymerization is too high, the amount of deposit tends to increase, and in a case where styrene is used as the raw material monomer, a dimer structure and a trimer structure form as by-products by heat polymerization characteristic to styrene.

The time for the former polymerization varies depending upon the temperature at the half life and the amount of use of the polymerization initiator, polymerizability of the monomer, the degree of crosslinking of the resin, etc., but is usually at least 2 hours, preferably at least 3 hours, more preferably at least 4 hours and usually at most 24 hours, preferably at most 12 hours, more preferably at most 8 hours. If the time for the former polymerization is too short, the polymerization will not be completed, or the amount of the remaining low molecular weight components and free polymer components can not be reduced. Further, if the time for the former polymerization is too long, the productivity tends to decrease.

On the other hand, as described above, in a case where an organic solvent is present in the reaction system (for example, production of a porous polymer), the polymerization reaction may be carried out in one stage since the above-described problem of deposition of an agglomerate at the lid of the reactor is less likely to arise.

(Introduction of Ion Exchange Groups)

The above weakly basic anion exchange resin is obtained by introducing ion exchange groups to the polymer (e.g. crosslinked polystyrene) obtained by the above-described polymerization.

Such an ion exchange group (anion exchange group) may, for example, be a quaternary ammonium group or a primary to tertiary amino group ($-N^+H_nR_{3-n}$) (wherein R is an optional substituent, and n is an integer of at least 1 and at most 3). Specific examples of the quaternary ammonium group and the primary to tertiary amino group include an ammonia group, a methylamino group, a dimethylamino group, a diethylamino group, an ethylenediamino group, a diethylenetriamino group, a triethylenetetramino group, a polyethyleneimine group, a butylenediamino group, a hexanediamino group and an ethanolamino group.

The above ion exchange groups may be introduced alone or may be introduced to the same polymer in optional combination of two or more types.

Introduction of the ion exchange groups may be carried out in accordance with a known method. A proper method may be selected depending upon the type of the substrate (the polymer in the present invention) to which they are introduced or the type of the ion exchange groups to be introduced.

For example, in the case of introducing primary to tertiary amino groups as weakly basic anion exchange groups, a means as disclosed in e.g. JP-A-2001-106725 may be employed.

Further, as a method of introducing weakly basic anion exchange groups, in addition to the above, a method may be mentioned wherein the substrate to which ion exchange groups are to be introduced is chloromethylated in accordance with a known method, and an amine such as diethylenetriamine, ethylenediamine, dimethylamine, diethylamine, monomethylamine, dibutylamine or piperazine or ammonia is added thereto for amination. By introduction of such substituents, the efficiency to remove noxious substances such as carbonyl compound will be higher.

It has been initially estimated that the mechanism of removing carbonyl compounds is only capturing by formation of a Schiff base by a primary amino group and a carbonyl compound. However, as a result of studies on the reaction mechanism, it was found that carbonyl compounds are captured not only by a weakly basic anion exchange resin having a primary amine, but also by such a resin having a secondary amine or a tertiary amine or by a strongly basic anion exchange resin having a trimethylammonium group with a high efficiency. The reason is estimated to be because aldol condensation and polymerization reaction of carbonyl compounds take place in addition to formation reaction of a Schiff base on the resin surface of the anion exchange resin. In other words, it is estimated that oligomerization of carbonyl compounds proceeds by a so-called basic catalyst.

In the ion exchange resin in general, micropores are present in a wet state, and gas components are diffused in them to conduct gas adsorption. If the degree of crosslinking of the ion exchange resin is high, the micropores tend to be small, and target molecules are hardly diffused and as a result, the capturing efficiency tends to decrease. On the other hand, if the degree of crosslinking is low, the pore structure hardly develops, whereby the target molecules are hardly diffused in the pores.

In the present invention, the moisture content of the gas adsorbent is from 3 to 20%, preferably from 5 to 20%, particularly preferably from 5 to 15%. When the moisture content is within the above range, the gas diffusibility in the micropores is properly maintained, whereby performance as the gas adsorbent can be maintained.

The moisture content of the gas adsorbent can be measured, for example, as follows.

(Measurement of Moisture Content)

A NaOH aqueous solution is brought into contact with the gas adsorbent as a test specimen to regenerate the anion exchange groups, followed by dehydration by proper apparatus such as a centrifugal separator, and a proper amount of the dehydrated gas adsorbent is weighed. The weighed gas adsorbent is further vacuum dried, and the mass of the vacuum dried gas adsorbent is measured. The moisture content in the gas adsorbent can be calculated from the mass after dehydration and the mass after vacuum drying. Further, the moisture content in the resin can be directly measured by a Karl Fischer moisture meter.

Further, as the adsorbent comprising an inorganic material such as silica, alumina or activated carbon as the base, preferred is one comprising such a base structure and primary to tertiary amino groups or quaternary ammonium groups fixed.

One comprising silica as the base and primary to tertiary amino groups or quaternary ammonium groups fixed may, for example, be a reaction product having 3-aminopropylsilyl groups introduced to silica gel particles, or a treated product obtained by subjecting one comprising particles of layered clay mineral comprising silicic acid as the main body and a double salt of a metal salt of Al and $N_2H_4$ supported on the surface of the particles, to elution treatment with an acid or to heat treatment at from 400° C. to 700° C.

The adsorbent comprising alumina impregnated with primary to tertiary amino groups or quaternary ammonium groups may, for example, be a carrier obtained by impregnating a silica or alumina carrier with a solution containing a polymerizable monomer, followed by polymerization, and as the case requires, introducing ion exchange groups. As the case requires, a polymerizable monomer having an ion exchange group may be used. For example, aminomethylstyrene or an aminoethyl (meth)acrylate monomer may, for example, be mentioned. Further, a polyfunctional polymerizable monomer may be added to the polymerizable monomer so as to reduce elution as far as possible.

An adsorbent comprising activated carbon impregnated with primary to tertiary amino groups or quaternary ammonium groups may, for example, be an adsorbent comprising an adsorptive composition comprising a phosphate of a tetravalent metal (including Group 4A elements such as titanium, zirconium, hafnium and thorium, and Group 4B elements such as germanium, tin and lead) and a hydroxide of a tetravalent metal (including e.g. Group 1B elements of the Periodic Table such as copper, Group 2A elements of the Periodic Table such as magnesium, calcium, strontium and barium, the Group 2B elements of the Periodic Table such as zinc and cadmium, the Group 6B elements of the Periodic Table such as chromium and molybdenum, Group 7A elements of the Periodic Table such as manganese, and the Group 8 elements of the Periodic Table such as iron, ruthenium, cobalt, rhodium, nickel and palladium) and sulfamic acid or a sulfamate supported on the adsorptive composition.

Further, an adsorbent comprising activated carbon and a cyclic saturated secondary amine and at least one member selected from a non-volatile acid, urea and thiourea supported on the activated carbon may, for example, be mentioned.

Further, a carrier obtained by impregnation with a solution containing a polymerizable monomer, followed by polymerization and as the case requires, introduction of ion exchange groups, similar to the silica or alumina carrier, may be mentioned. As the case requires, a polymerizable monomer having an ion exchange group may be used. For example, aminomethylstyrene or an aminoethyl (meth)acrylate monomer may be mentioned. Further, a polyfunctional polymerizable monomer may be added to the polymerizable monomer so as to reduce elution as far as possible.

Further, an adsorbent comprising a porous material such as activated carbon impregnated with aminobenzenesulfonic acid and hydrogen phosphate and/or phosphoric acid so that the impregnation ratio of the hydrogen phosphate and/or phosphoric acid is 0.2 to 6 mol per mol of the aminobenzenesulfonic acid may, for example, be mentioned.

Further, an adsorbent comprising activated carbon impregnated with ethylenediamine and/or triethanolamine, comprising activated carbon impregnated with ethylenediamine phosphate and/or triethanolamine phosphate, or comprising activated carbon impregnated with phosphoric acid and having ethylenediamine and/or triethanolamine added thereto to be impregnated with an amine phosphate, may, for example, be mentioned.

Further, an adsorbent comprising an activated carbon material impregnated with a primary or secondary amine having an aliphatic group having a vapor pressure of at most 5 mmHg at 20° C., or an adsorbent comprising an activated carbon material impregnated with a polyalkyleneimine having a number average molecular weight of from 250 to 3,000, such as polyethyleneimine, in an amount of from 1 to 50 wt %, preferably from 5 to 30 wt %, may, for example, be mentioned.

The gas adsorbent of the present invention as described above efficiently removes acidic noxious substances such as hydrogen cyanide and hydrogen sulfide present in cigarette smoke from a high flow rate gas stream and hardly releases bad odor components such as amine impurities and free noxious components such as a monocyclic aromatic compound derived from the gas adsorbent itself into gas which passed through the gas adsorbent.

Accordingly, the gas adsorbent of the present invention is generally used for a gas filter or equipment for removal of noxious gas, particularly suitably used for a cigarette filter or a gas filter of apparatus which is required to remove noxious gas in cigarette smoke such as an air cleaner or a car air conditioner.

In a case where the gas adsorbent of the present invention is used for a cigarette filter, not only noxious substances are efficiently removed from smoke which passes through the cigarette filter at the time of smoking but also the flavor of a cigarette is hardly impaired or the health is less likely to be damaged due to bad odor components and noxious components derived from the gas adsorbent itself.

Further, when the gas adsorbent of the present invention is used for a gas filter of apparatus which is required to remove noxious gas in cigarette smoke such as an air cleaner or a car air conditioner, not only noxious substance is efficiently removed from the air taken in at a high rate, but also the air discharged from the apparatus does not contain bad odor components and noxious components derived from the gas adsorbent itself. Accordingly, the gas adsorbent itself is less likely to impair unpleasant sensation to the user of the apparatus or to harm health of the user of the apparatus.

The gas adsorbent of the present invention is typically used in the form of the gas filter as supported on a support having a large surface area such as porous particles or highly air permeable fiber aggregates, but it may be used in the form other than a gas filter so long as gas to be treated containing noxious gas is to be in contact with the gas adsorbent of the present invention. In a case where the gas adsorbent of the present invention is used as a cigarette filter, usually, fine particles of the gas adsorbent of the present invention or fine particles having the gas adsorbent of the present invention supported thereon are added to fibers for a cigarette filter.

Further, it is preferred to use the gas adsorbent itself as processed into fine particles having a very small particle size or into porous particles, in order that the area of contact between the gas adsorbent of the present invention and gas to be treated is large.

Further, the adsorbent of the present invention may be used alone or may be used in combination with another gas adsorbent.

Further, it is preferred to use the gas adsorbent itself as processed into fine particles having a very small particle size or into porous particles, in order that the area of contact between the gas adsorbent of the present invention and gas to be treated is large.

EXAMPLES

Now, the present invention will be described in further detail with reference to Examples. The test methods conducted in the present Examples are as follows.

(1) Amine Elution Test 50 g of a resin (gas adsorbent) drained by a centrifugal separator was packed in a column having an inner diameter of 15 mm using deionized water. 5 BV of a 2N HCl aqueous solution was made to pass through the column at SV1 ("SV" means the volume flow rate (L/h) per hour per liter of the resin (gas adsorbent)), and the eluant was recovered. The absorbance (wavelength: 254 nm) of the recovered eluant was measured and further, the eluant was analyzed by ion chromatography and high performance liquid chromatography (HPLC) under the following conditions.

HPLC analysis: column ODS column, elution with a gradient of 5%/min from a 50% acetonitrile aqueous solution to a 100% acetonitrile solution. UV detector, measurement wavelength: 254 nm.

(2) Measurement of Pore Physical Properties (Pore Radius, Pore Volume, Surface Area)

A vacuum dried resin (gas adsorbent) was put in a glass cell, and the pore radius and the pore volume of the resin were measured by a mercury porosimeter (Autopore 9220, manufactured by Shimadzu Corporation). From a histogram showing the distribution of pores indicating the measured pore volume and pore radius respectively by the vertical axis and the horizontal axis, the pore radius at a portion with the largest total pore volume was regarded as the mean pore radius.

Further, the surface area of the resin (gas adsorbent) was measured by a nitrogen adsorption method (FlowSorb 2300 model, manufactured by Micrometrics).

In Tables, a surface area of 0 means no pores were confirmed or substantially no pores were confirmed.

(3) Aromatic Compound Elution Test 50 g of a resin (gas adsorbent) drained by a centrifugal separator was packed in a column having an inner diameter of 15 mm using deionized water. 5 BV of isopropyl alcohol was made to flow through the column at room temperature at a rate of SV1, and the eluant was recovered. The recovered eluant was analyzed by gas chromatography (GC) and HPLC to measure contents of toluene, styrene, ethylvinylbenzene, divinylbenzene, diethylbenzene and phenol. GC analysis conditions and HPLC analysis conditions were as follows.

GC analysis conditions: column HP-5 (manufactured by HP), the temperature was raised from 50° C. to 250° C. at a rate of 10° C./min. Helium was used as the carrier gas. FID detector.

HPLC analysis: column ODS column, elution with a gradient of 5%/min from a 50% acetonitrile aqueous solution to a 100% acetonitrile solution, after a lapse of 10 minutes, maintenance for 5 minutes with a 100% acetonitrile solution for 5 minutes. UV Detector, measurement wavelength: 254 nm.

(4) Acidic Component Adsorption Test 10.0 ml of a gas adsorbent was collected in a measuring cylinder and packed in a glass column, and 200 ml of a 2 N hydrochloric acid aqueous solution was made to flow, followed by washing with deionized water. Then, 250 ml of a 2 N sodium hydroxide aqueous solution was made to pass. Further, deionized water was made to flow until the eluant became neutral. The resin was put in a 500 ml Erlenmeyer flask, and 300 ml of a 0.2 N HCl aqueous solution was added, followed by shaking for 8 hours. After shaking, 20.0 ml of the supernatant liquid was sampled by a whole pipette and titrated with a 0.1 N NaOH aqueous solution, and the amount of adsorbed hydrochloric acid was calculated as a value per volume to determine the acid adsorption capacity.

(5) Measurement of Neutral Salt Decomposition Capacity

An anion exchange resin (gas adsorbent) was put in a column, and a 5% NaCl aqueous solution in an amount of 25 times the resin capacity was made to flow to convert counter ions to Cl form. 10.0 ml of the resin was weighed, and a 2 N NaOH aqueous solution in an amount of 75 times was made to flow to regenerate the Cl form to OH form. The resin was sufficiently washed with deionized water until the filtrate used for washing became neutral, and then a 5% NaCl aqueous solution in an amount of 25 times was made to flow, and all the eluant was collected. The eluant was titrated with hydrochloric acid to calculate the neutral salt decomposition capacity.

(6) Propionaldehyde Adsorption Test 10.0 g of a resin (gas adsorbent) was added to a 200 ml Erlenmeyer flask, and 50.0 g of a propionaldehyde solution at a concentration of 2.0 wt % in a 10% methanol (MeOH) aqueous solution as a solvent was added, followed by shaking at room temperature for one day. After completion of shaking, the supernatant liquid was sampled to calculate the adsorption amount of propionaldehyde by means of gas chromatography (GC) under the following conditions.

GC analysis conditions: Column HP-5 (manufactured by HP), analyzed at a constant temperature of 50° C. Holding time: 2.512 minutes. Helium was used as the carrier gas. FID detector.

(7) Aldehyde Adsorption Rate Test 5.00 g of a resin (gas adsorbent) in a drained state was put in a 300 ml Erlenmeyer flask, and 100.0 ml of a propionaldehyde aqueous solution preliminarily adjusted to a concentration of 100 ppm at a temperature of 25.0° C. was instantaneously injected thereinto, followed by shaking by a shaker set at 25.0° C. under conditions under which the resin was maintained in a suspended state. 3 Minutes and 10 minutes after injection of the propionaldehyde aqueous solution, the supernatant liquid was sampled to calculate the concentration of propionaldehyde by means of gas chromatography (GC). The GC analysis conditions were as follows.

GC analysis conditions: column HP-5 (manufactured by HP), analyzed at a constant temperature of 30° C. Holding time: about 2.51 minutes. Amount of sample injected: 5.0 µl, split ratio: 25:1, FID detector.

(8) Nicotinamide Adsorption Test 10.0 g of a resin (gas adsorbent) was added to a 200 ml Erlenmeyer flask, and 50.0 g of a 1 wt % nicotinamide aqueous solution was added, followed by shaking at room temperature for one day. After completion of shaking, the supernatant liquid was sampled to measure the concentration of nicotinamide by HPLC under the following conditions.

HPLC analysis conditions: liquid A (10% acetonitrile aqueous solution), liquid B (70% acetonitrile aqueous solution). Elution with a gradient of 10%/min from the liquid A to the liquid B. Maintenance for 3 minutes with a 70% acetonitrile aqueous solution. The holding time of nicotinamide was 4.4 minutes. The peak was detected at UV 254 nm, and the concentration of nicotinamide was measured from an analytical curve.

(9) 1-Menthol Adsorption Test 10.0 g of a resin (gas adsorbent) was added to a 200 ml Erlenmeyer flask, and 50.0 g of a 2 wt % 1-menthol aqueous solution based on a 50 wt % methanol aqueous solution was added, followed by shaking at room temperature for one day. After completion, the supernatant liquid was sampled to measure the concentration of 1-menthol by means of gas chromatography (GC) under the following conditions.

GC analysis conditions: column HP-5 (manufactured by HP), the temperature was raised from 50° C. to 250° C. at 1° C./min. The holding time of 1-menthol was 10.8 minutes, and the peak was detected by a FID detector, and the concentration of 1-menthol was measured from an analytical curve to calculate the adsorption amount.

(10) Reference Test: Gaseous Phase Gas Capturing Test

In order to confirm that the above-described (6) propionaldehyde adsorption test and (7) aldehyde adsorption rate test properly represent the gas capturing performance in a gaseous phase system, the following gaseous phase system gas capturing test was carried out in some of Examples and Comparative Examples described hereinafter. A preferred gas adsorption ratio as a gas adsorbent is considered to be usually at least 40%, preferably at least 45%.

40 mg of a vacuum dried adsorbent and 100 mg of glass beads (AS ONE Corporation, BZ-06) were packed in a quartz tube having an inner diameter of 8.0 mm (outer diameter of 10.0 mm), and both ends were filled with glass wool and fixed. At the inlet of the tube packed with the adsorbent (the resin packed layer: 8.0 mm in diameter×4.0 mm), a tetrabag in which a 1,000 volppm acetaldehyde gas (1.0% acetaldehyde standard gas was diluted with nitrogen gas; the quantitative determination method was internal standard method; 100 ppm of methane gas was added to acetaldehyde gas, and acetaldehyde was quantitatively determined employing methane gas as a standard) was put was attached, and a 100 ml gas syringe and a GC apparatus were connected at the outlet by means of a three-way valve. The gas tight syringe was pulled at 35 ml/2 seconds by a low speed cylinder unit to aspirate gas in the quartz glass tube. The adsorption temperature was from 24° C. to 26° C. After aspiration, the valve was shifted to send the aspirated gas to GC, and acetaldehyde which was not adsorbed was quantitatively determined by GC. This operation was repeated every 5 minutes ten times to evaluate the adsorption ratio (%) and the adsorption behavior.

As gas chromatography, GC-14A manufactured by Shimadzu Corporation was used. DB-WAX column (0.53 mm in diameter×32 mm) was used as the column, the analysis temperature was 60° C., the column inlet temperature was 50° C., the detector temperature was 50° C., and a FID detector was used as the detector.

(11) Measurement of Number Average Particle Size

Sieves with a screen mesh of 1,180 μm, 850 μm, 710 μm, 600 μm, 425 μm and 300 μm are overlaid so that the screen mesh size was smallest at the bottom. The overlaid sieves were placed on a vat, and about 100 mL of the gas adsorbent was put in the sieve of 1,180 μm on top of the pile.

Water was slowly poured on the resin from a rubber tube connected to water works to remove small particles downward by sieving. From the gas adsorbent remaining in the sieve of 1,180 μm, small particles were further removed by sieving strictly by the following method. Namely, another vat was filled with water to about half the depth, and the sieve of 1,180 μm was repeatedly shaken by imparting up-and-down and rotational motions in the vat to remove small particles by sieving.

The small particles in the vat were recovered to the second largest sieve of 850 μm, and the gas adsorbent remaining on the sieve of 1,180 μm was collected in another vat. If the screen mesh was clogged with the gas adsorbent, the sieve was put on a vat upside down, a rubber tube connected to water works was closely contacted, and the gas adsorbent in the screen mesh was taken out by fast running water. The taken out gas adsorbent was transferred to the vat in which the gas adsorbent remaining on the sieve of 1,180 μm was collected, and the total volume was measured by a measuring cylinder, which was regarded as "a" (mL). The anion exchange resin which passed through the sieve of 1,180 μm was subjected to the same operation regarding the sieves of 850 μm, 710 μm, 600 μm, 425 μm and 300 μm, volumes b (mL), c (mL), d (mL), e (mL) and f (mL) were obtained by using a measuring cylinder, and finally, the volume of the resin which passed through the sieve of 300 μm was measured by a measuring cylinder and regarded as g (mL).

Assuming V=a+b+c+d+e+f+g, a/×100=a'(%) b/×100=b' (%), c/×100=c'(%), d/×100=d'(%) e/×100=e'(%), f/×100=f' (%) and g/×100=g'(%) were calculated.

From the above a' to g', the sum total (%) of the residue on the respective sieves was plotted on one axis and the size (mm) of the screen mesh was plotted on the other axis, which were plotted on logarithmic probability paper. Three points of first to third largest residue were taken, and a line which satisfies these three points as far as possible was drawn, from which the size (mm) of the screen mesh corresponding to a sum total of the residue of 50% was determined, which was regarded as the number average particle size.

Example 1

DIAION (registered trademark) CR20 (tradename, amino group-containing weakly basic anion exchange resin manufactured by Mitsubishi Chemical Corporation) was drained by a center, and 100 ml thereof was weighed and put in a 1 L four-necked flask equipped with a condenser tube and an agitating blade. 400 ml of a 2 N HCl aqueous solution was added thereto, followed by stirring at 80° C. for 5 hours. The solution was drawn, and 400 ml of a 2 N HCL aqueous solution was newly added, followed by stirring further for 5 hours and washing.

The flask was cooled to room temperature, the above resin was packed in a glass column, and 5 BV of a 1 N HCl aqueous solution was made to flow at room temperature at SV1. After washing with a 1 N HCl aqueous solution, 10 BV of deionized water was made to flow for washing to remove an excessive hydrochloric acid solution.

While the ion exchange groups of the resin in the column after washing remained in the Cl form, 5 BV of methanol was made to flow at room temperature at SV1. 5 BV of deionized water was further made to flow to remove methanol.

BV of a 1 N NaOH aqueous solution was made to flow through the resin to ion-exchange the ion exchange groups of the resin in the column to OH form (free form), and finally, 5 BV of deionized water was made to flow, and the obtained resin was subjected to tests as a gas adsorbent (amino group-containing weakly basic anion exchange resin) in Example 1.

Example 2

A chloromethylated polymer having a structure represented by the following formula 2 as the main skeleton, which is a precursor of DIAION (registered trademark) CR20 (tradename, amino group-containing weakly basic anion exchange resin manufactured by Mitsubishi Chemical Corporation), washed in the same manner as in Example 1 (up to a stage of removing an excessive hydrochloric acid solution by washing with a 1 N HCl aqueous solution and making 10 BV of deionized water to flow) (hereinafter referred to as a "washed precursor"), was aminated as follows.

50 g of the above-obtained washed precursor was weighed in a 500 ml four-necked flask equipped with a condenser tube and an agitating blade, and 250 ml of deionized water was added, followed by stirring at room temperature for one hour. 30 g of a 45% sodium hydroxide aqueous solution and 70 g of a 50% dimethylamine aqueous solution were added thereto, followed by stirring at 50° C. for 5 hours. After the reaction, the resin was taken out, packed in a glass column and washed with 20 BV of deionized water, and the amine used for the reaction was removed, and the obtained resin was subjected to tests as a gas adsorbent (amino group-containing weakly basic anion exchange resin) in Example 2.

Formula 2:

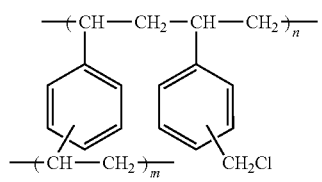

wherein each of m and n is an integer of at least 1.

Example 3

The same washed precursor used in Example 2 was aminated as follows.

50 g of the above washed precursor was put in a 500 ml four-necked flask equipped with a condenser tube and an agitating blade, and 150 ml of deionized water, 30 g of a 45% sodium hydroxide aqueous solution and 200 g of diethylenetriamine (DETA, manufactured by Tokyo Chemical Industry Co., Ltd.) were added, followed by stirring at 120° C. for 5 hours. After the reaction, the resin was taken out, packed in a glass column and washed with 20 BV of deionized water, and the amine used for the reaction was removed, and the obtained resin was subjected to tests as a gas adsorbent (amino group-containing weakly basic anion exchange resin) in Example 3.

Example 4

The same washed precursor used in Example 2 was aminated as follows.

50 g of the above washed precursor was put in a 500 ml four-necked flask equipped with a condenser tube and an agitating blade, 100 ml of deionized water, 44 g of a 45% sodium hydroxide aqueous solution and 49 g of DETA were added, and the temperature was raised from room temperature to 120° C., followed by stirring at 120° C. for 5 hours. After the reaction, the resin was taken out, and the resin was washed with deionized water until the solution became neutral. Then, the resin was subjected to purification treatment in the same manner as in Example 1, and the obtained resin was subjected to tests as a gas adsorbent (amino group-containing weakly basic anion exchange resin) in Example 4.

Example 5

A resin treated in the same manner as in Example 4 except that the weight of DETA charged was changed from 49 g to 12.25 g was subjected to tests as a gas adsorbent (amino group-containing weakly basic anion exchange resin) in Example 5.

Example 6

A resin treated in the same manner as in Example 4 except that the weight of DETA charged was changed from 49 g to 6.12 g was subjected to tests as a gas adsorbent (amino group-containing weakly basic anion exchange resin) in Example 6.

Examples 7, 8 and 9

The gas adsorbent obtained in Example 1 was classified into three stages by sieving. The number average particle sizes of the resins at the respective stages were 550 μm, 760 μm and 380 μm, respectively.

Such resins were dried by a vacuum dryer until the moisture content became about 10%. Then, each resin was put in a constant temperature and constant humidity chamber at 25° C. under a relative humidity of 75% for 3 days for moisture conditioning. During the moisture conditioning, the resin was periodically moved and mixed. The resins after moisture conditioning had a moisture content of about 12.5% and had number average particle sizes of 510 μm, 700 μm and 350 μm, respectively.

The gas adsorbent having a number average particle size of 510 μm as a gas adsorbent (amino group-containing weakly basic anion exchange resin) in Example 7, the gas adsorbent having a number average particle size of 700 μm as a gas adsorbent (amino group-containing weakly basic anion exchange resin) in Example 8 and a gas adsorbent having a number average particle size of 350 μm as a gas adsorbent (amino group-containing weakly basic anion exchange resin) in Example 9 were respectively subjected to tests.

Example 10

To a 3 L SUS pressure reactor equipped with an agitating blade, a nitrogen introduction tube, a pressure gauge, a pressure sensor and a protective tube for a thermometer, the following organic phase and aqueous phase were added.

Organic phase: an aqueous solution of 83.9 g of 63% divinylbenzene (DVB), 129.5 g of styrene, 254.7 g of isooctane, 1.28 g of benzoyl peroxide (BPO) having a purity of 75% and 1.185 g of PBZ (t-butyl perbenzoate, manufactured by NOF Corporation) was prepared.

Aqueous phase: 985 ml of deionized water, 53.3 ml of a 3% polyvinyl alcohol solution and 21 ml of a 0.1% $NaNO_2$ aqueous solution were prepared.

Then, the reactor was depressurized to 5 kPa with stirring by the reaction blade, and then 0.3 MPa of nitrogen gas was injected. This operation was repeated five times, and further, nitrogen gas was bubbled with stirring at 200 ml/min for 15 minutes to remove dissolved oxygen in the reactor to 0.1 ppm or below.

The reactor was adjusted to a temperature of 25° C., followed by stirring at 120 rpm for one hour. Then, stirring was carried out at 80° C. for 4 hours, and further the temperature was raised to 115° C., followed by stirring for 4 hours. The pressure at 80° C. was 0.09 MPa, and the pressure at 115° C. was 0.25 MPa. The reactor was cooled, and the resin was taken out and washed with deionized water to obtain a white resin which smelled slightly of isooctane.

200 g of the resin was put in a 2 L four-necked flask equipped with an agitating blade and a condenser tube, and isooctane remaining in the resin was removed by steam distillation.

At this stage, a resin having a moisture content of 59.5%, a specific surface area of 34 m$^2$/g, a mean pore radius of 1,101 Å and a pore volume of 1.67 ml/g was obtained. The polymer yield was at least 99.5%. Further, the amount of styrene remaining in the resin was 1.2 ppm, the amount of ethylvinylbenzene (EVB) was 0.4 ppm, and the amount of DVB was 0.1 ppm.

300 g of chloromethyl methyl ether was added to 50 g of the resin obtained by the above procedure, followed by stirring at 50° C. for one hour. The resin was chloromethylated by addition of 15 g of zinc chloride, and then aminated in the same manner as in Example 2, and the obtained resin was subjected to tests as a gas adsorbent (amino group-containing weakly basic anion exchange resin) in Example 10.

Example 11

To a 3 L SUS pressure reactor equipped with an agitating blade, a nitrogen introduction tube, a pressure gauge, a pressure sensor and a protective tube for a thermometer, the following organic phase and aqueous phase were added.

Organic phase: a solution of 138.5 g of 63% divinylbenzene, 210.6 g of styrene, 419 g of toluene, 1.16 g of benzoyl peroxide having a purity of 75% and 0.87 g of PBZ (t-butyl perbenzoate, manufactured by NOF Corporation) was prepared.

Aqueous phase: 1,624 ml of deionized water, 51.3 ml of a 3% polyvinyl alcohol solution and 34 ml of a 0.1% NaNO$_2$ aqueous solution were prepared.

Then, the reactor was depressurized to 5 kPa with stirring by the reaction blade, and then 0.3 MPa of nitrogen gas was injected. This operation was repeated five times, and further, nitrogen gas was bubbled with stirring at 200 ml/min for 15 minutes to remove dissolved oxygen in the reactor to 0.2 ppm or below.

The reactor was adjusted to a temperature of 25° C., followed by stirring at 115 rpm for one hour. Then, the temperature was raised from room temperature to 80° C., followed by stirring for 4 hours, and further the temperature was raised to 120° C., followed by polymerization for 4 hours. The reactor was cooled, and the resin was taken out and washed with toluene. This operation was repeated four times.

200 g of the resin was put in a 2 L four-necked flask equipped with an agitating blade and a condenser tube, and toluene remaining in the resin was removed by steam distillation. Then, the resin was aminated in the same manner as in Example 2 to obtain a gas adsorbent (weakly basic anion exchange resin) in Example 11, was subjected to tests as a gas adsorbent (amino group-containing weakly basic anion exchange resin) in Example 11.

Example 12

The same washed precursor used in Example 2 was aminated as follows.

50 g of the above washed precursor was put in a 500 ml four-necked flask equipped with a condenser tube and an agitating blade, 80 ml of deionized water, 44 g of a 45% sodium hydroxide aqueous solution, 19.6 g of DETA and 75 g of toluene were added, and the temperature was raised to 80° C., followed by stirring for 5 hours.

After the reaction, the resin was taken out and washed with deionized water until the solution became neutral. The obtained resin was put in a 1 L flask equipped with a stirrer and a distillation apparatus, 0.5 L of deionized water was added, and steam distillation was carried out at a bath temperature of 110° C. (internal temperature of 108° C.). As water was distilled off, deionized water was dropped to maintain the liquid level constant. Toluene remaining in the resin was removed by such steam distillation. Further, the resin was purified to remove toluene by the procedure shown in Example 1. Then, the resin was aminated in the same manner as in Example 2 to obtain a gas adsorbent (amino group-containing weakly basic anion exchange resin) in Example 12.

Example 13

To a 3 L SUS pressure reactor equipped with an agitating blade, a nitrogen introduction tube, a pressure gauge, a pressure sensor and a protective tube for a thermometer, the following organic phase and aqueous phase were added.

Organic phase: a solution of 143.7 g of 63% divinylbenzene, 221.9 g of styrene, 438.9 g of toluene, 95.1 g of polystyrene (molecular weight: 48,000), 2.44 g of benzoyl peroxide having a purity of 75% and 1.87 g of PBZ (t-butyl perbenzoate, manufactured by NOF Corporation) was prepared.

Aqueous phase: 1,678 ml of deionized water, 91.4 ml of a 3% polyvinyl alcohol aqueous solution and 36 ml of a 0.1% NaNO$_2$ aqueous solution were prepared.

Then, the reactor was depressurized to 5 kPa with stirring by the reaction blade, and 0.3 MPa of nitrogen gas was injected. This operation was repeated five times, and further, nitrogen gas was bubbled with stirring at 200 ml/min for 15 minutes to remove dissolved oxygen in the reactor to 0.1 ppm or below. The reactor was adjusted to a temperature of 25° C., followed by stirring at 120 rpm for one hour. Then, the temperature was raised to 80° C. and maintained for 4 hours. The temperature was further raised to 120° C., followed by stirring for 4 hours. The pressure at 80° C. was 0.072 MPa, and the pressure at 120° C. was 0.29 MPa. The reactor was cooled, and the resin was taken out and washed with deionized water to obtain a white resin.

200 g of the resin was packed in a glass column, and toluene in an amount five times was made to flow to remove added polystyrene. Then, the obtained resin was put in a 2 L four-necked flask equipped with an agitating blade and a condenser tube, and toluene remaining in the is resin was removed by steam distillation. At this stage, a resin having a specific surface area of 50 m$^2$/g, a mean pore radius of 753 Å and a pore volume of 0.99 ml/g was obtained. The polymer yield was at least 97.8%. 300 g of chloromethyl methyl ether was added to 50 g of the dry resin obtained by the above procedure, followed by stirring at 25° C. for one hour. 60 g of zinc chloride was added, and the temperature was raised to 50° C., followed by stirring for 5 hours for chloromethylation. The above chloromethylated polymer wet with water, drained by a center (5 minutes), was put in a 1 L four-necked flask, 325 ml of deionized water was put, and 438 g of a 48% NaOH aqueous solution was put with stirring. Then, 49.7 g of diethylenetriamine (DETA, manufactured by Tokyo Chemical Industry Co., Ltd.) was put. The temperature was raised from room temperature to a bath temperature of 115° C. (internal temperature of 110° C.) over a period of 2 hours, followed by stirring for 5 hours. After completion, the resin was taken out, and the reaction solution was drawn, followed by batch washing with deionized water. This operation was repeated three times, and then the resin was put in a glass column, and deionized water was made to flow until neutral, and the obtained resin was subjected to tests as a gas adsorbent (amino group-containing weakly basic anion exchange resin) in Example 13.

Example 14

A resin treated in the same manner as in Example 13 except that the weight of DETA charged was changed from 49.7 g to 31.1 g was subjected to tests as a gas adsorbent (amino group-containing weakly basic anion exchange resin) in Example 14.

Example 15

A resin treated in the same manner as in Example 13 except that the weight of DETA charged was changed from 49.7 g to 15.5 g was subjected to tests as a gas adsorbent (amino group-containing weakly basic anion exchange resin) in Example 15.

Example 16

A resin treated in the same manner as in Example 13 except that the weight of DETA charged was changed from 49.7 g to 10.4 g was subjected to tests as a gas adsorbent (amino group-containing weakly basic anion exchange resin) in Example 16.

Example 17

To a 2 L SUS pressure reactor equipped with an agitating blade, a nitrogen introduction tube, a pressure gauge, a pressure sensor and a protective tube for a thermometer, the following organic phase and aqueous phase were added.

Organic phase: a solution of 83.9 g of 63% divinylbenzene, 129.5 g of styrene, 202.7 g of isooctane, 1.28 g of benzoyl peroxide having a purity of 75% and 1.185 g of PBZ (t-butyl perbenzoate, manufactured by NOF Corporation) was prepared. Aqueous phase: 985 ml of deionized water, 53.3 ml of a 3% polyvinyl alcohol aqueous solution and 21 ml of a 0.1% $NaNO_2$ aqueous solution were prepared.

Then, the reactor was depressurized to 5 kPa with stirring by the reaction blade, and then 0.3 MPa of nitrogen gas was injected. This operation was repeated five times, and further, nitrogen gas was bubbled with stirring at 200 ml/min for 15 minutes to remove dissolved oxygen in the reactor to 0.1 ppm or below.

The reactor was adjusted to a temperature of 25° C., followed by stirring at 120 rpm for one hour. Then, stirring was carried out at 80° C. for 4 hours, and further the temperature was raised to 115° C., followed by stirring for 4 hours. The pressure at 80° C. was 0.088 MPa, and the pressure at 115° C. was 0.28 MPa. The reactor was cooled, and the resin was taken out and washed with deionized water to obtain a white resin which smelled slightly of isooctane.

200 g of the resin was put in a 2 L four-necked flask equipped with an agitating blade and a condenser tube, and isooctane remaining in the resin was removed by steam distillation.

At this stage, a resin having a specific surface area of 53 $m^2/g$, a mean pore radius of 472 Å and a pore volume of 1.42 ml/g was obtained.

50 g of the resin obtained by the above procedure was chloroemthylated and aminated with DETA in the same manner as in Example 13 except that the weight of DETA charged was changed from 49.7 g to 124.2 g, and the obtained resin was subjected to tests as a gas adsorbent (amino group-containing weakly basic anion exchange resin) in Example 17.

Example 18

The same operation as in Example 17 was carried out except that the weight of isooctane charged was changed from 202.7 g to 211.3 g to obtain a white resin which smelled slightly of isooctane.

Then, at the stage after removal of isooctane remaining in the resin, a resin having a specific surface area of 44 $m^2/g$, a mean pore radius of 603 Å and a pore volume of 1.48 ml/g was obtained. 50 g of the resin obtained by the above procedure was chloromethylated and aminated in the same manner as in Example 17, and the obtained resin was subjected to tests as a gas adsorbent (amino group-containing weakly basic anion exchange resin) in Example 18.

Example 19

The same operation as in Example 17 was carried out except that the weight of isooctane charged was changed from 202.7 g to 224.1 g to obtain a white resin which smelled slightly of isooctane.

Then, at the stage after removal of isooctane remaining in the resin, a resin having a specific surface area of 34 $m^2/g$, a mean pore radius of 1,101 Å and a pore volume of 1.67 ml/g was obtained.

50 g of the resin obtained by the above procedure was chloromethylated and aminated in the same manner as in Example 17, and the obtained resin was subjected to tests as a gas adsorbent (amino group-containing weakly basic anion exchange resin) in Example 19.

Example 20

To a 3 L SUS pressure reactor equipped with an agitating blade, a nitrogen introduction tube, a pressure gauge, a pressure sensor and a protective tube for a thermometer, the following organic phase and aqueous phase were added.

Organic phase: a solution of 50.8 g of 63% divinylbenzene, 353.4 g of styrene, 303.2 g of isooctane, 1.90 g of benzoyl peroxide having a purity of 75% and 1.60 g of PBZ (t-butyl perbenzoate, manufactured by NOF Corporation) was prepared.

Aqueous phase: 1,492 ml of deionized water, 67.1 ml of a 3% polyvinyl alcohol aqueous solution and 31.8 ml of a 0.1% $NaNO_2$ aqueous solution were prepared.

Then, the reactor was depressurized to 5 kPa with stirring by the reaction blade, and 0.3 MPa of nitrogen gas was injected. This operation was repeated five times, and further, nitrogen gas was bubbled with stirring at 200 ml/min for 15 minutes to remove dissolved oxygen in the reactor to 0.1 ppm or below.

The reactor was adjusted to a temperature of 25° C., followed by stirring at 120 rpm for one hour. Then, stirring was carried out at 80° C. for 4 hours, and the temperature was further raised to 115° C., followed by stirring for 4 hours. The pressure at 80° C. was 0.088 MPa, and the pressure at 115° C. was 0.27 MPa. The reactor was cooled, and the resin was taken out and washed with deionized water to obtain a white resin which smelled slightly of isooctane.

200 g of the resin was put in a 2 L four-necked flask equipped with an agitating blade and a condenser tube, and isooctane remaining in the resin was removed by steam distillation. 150 g of chloromethyl methyl ether and 150 g of 1,2-dichloroethane were added to 50 g of the obtained dry resin, followed by stirring at 25° C. for one hour. 35 g of iron chloride was added, and the temperature was raised to 50° C., followed by stirring for 8 hours for chloromethylation. The above chloromethylated polymer wet with water, drained by a center (5 minutes), was put in a 1 L four-necked flask, 325 ml of deionized water and 225 ml of toluene were put, and 438 g of a 48% NaOH aqueous solution was put with stirring. Then, 21.6 g of ethylenediamine was put. The temperature was raised from room temperature to a bath temperature of 82° C. (internal temperature of 80° C.) over a period of 2 hours, followed by stirring for 6 hours. After completion, the resin was taken out and put in another flask, and toluene was removed by steam distillation. The resin was put in a glass column, and deionized water was made to flow until neutral, and the obtained resin was subjected to tests as a gas adsorbent (amino group-containing weakly basic anion exchange resin) in Example 20.

Example 21

A resin chloromethylated and aminated in the same manner as in Example 20 except that the weight of the 68% divinylbenzene charged was changed from 50.8 g to 38.1 g and the weight of styrene charged was changed from 353.4 g to 366.1 g, was subjected to tests as a gas adsorbent (amino group-containing weakly basic anion exchange resin) in Example 21.

Example 22

To a 3 L SUS pressure reactor equipped with an agitating blade, a nitrogen introduction tube, a pressure gauge, a pressure sensor and a protective tube for a thermometer, the following organic phase and aqueous phase were added.

Organic phase: a solution of 95.3 g of 63% divinylbenzene, 308.9 g of styrene, 364 g of n-heptane, 1.70 g of benzoyl peroxide having a purity of 75% and 1.53 g of PHD (PERHEXYL D, manufactured by NOF Corporation) was prepared.

Aqueous phase: 1,664 ml of deionized water, 67.4 ml of a 3% polyvinyl alcohol aqueous solution and 35.3 ml of a 0.1% $NaNO_2$ aqueous solution were prepared.

Then, the reactor was depressurized to 5 kPa with stirring by the reaction blade, and 0.3 MPa of nitrogen gas was injected. This operation was repeated five times, and further, nitrogen gas was bubbled with stirring at 200 ml/min for 15 minutes to remove dissolved oxygen in the reactor to 0.1 ppm or below.

The reactor was adjusted to a temperature of 25° C., followed by stirring at 120 rpm for one hour. Then, stirring was carried out at 80° C. for 4 hours, and then the temperature was further raised to 130° C., followed by stirring for 6 hours. The pressure at 80° C. was 0.093 MPa, and the pressure at 130° C. was 0.46 MPa. The reactor was cooled, and the resin was taken out and washed with deionized water to obtain a white resin which smelled slightly of n-heptane.

200 g of the resin was put in a 2 L four-necked flask equipped with an agitating blade and a condenser tube, and n-heptane remaining in the resin was removed by steam distillation. 150 g of chloromethyl methyl ether and 150 g of 1,2-dichloroethane were added to 50 g of the obtained dry resin, followed by stirring at 25° C. for one hour. 35 g of iron chloride was added, and the temperature was raised to 50° C., followed by stirring for 8 hours for chloromethylation. The above chloromethylated polymer wet with water, drained by a center (5 minutes), was put in a 1 L four-necked flask, 325 ml of deionized water and 225 ml of toluene were put, and 438 g of a 48% NaOH aqueous solution was put with stirring. Then, 32.7 g DETA was put. The temperature was raised from room temperature to a bath temperature of 82° C. (internal temperature of 80° C.) over a period of 2 hours, followed by stirring for 6 hours. After completion, the resin was taken out and put in another flask, and toluene was removed by steam distillation. The resin was put in a glass column, and deionized water was made to flow until neutral, and the obtained resin was subjected to tests as a gas adsorbent (amino group-containing weakly basic anion exchange resin) in Example 22.

Example 23

A resin treated in the same manner as in Example 16 except that the amination conditions were changed as follows, was subjected to tests as a gas adsorbent (amino group-containing weakly basic anion exchange resin) in Example 23. Namely, 140 g of a polymer wet with water, drained by a center (5 minutes) was put in a 1 L four-necked flask, 200 ml of dimethoxymethane was put, and 438 g of a 48% NaOH was put with stirring. Then, 10.4 g of DETA was put. The temperature was raised from room temperature to a bath temperature of 45° C. (internal temperature of 43° C.) over a period of 30 minutes, followed by stirring for 5 hours. After completion, the resin was taken out, and a reaction solution was drawn, followed by batch washing with deionized water. This operation was repeated three times, the resin was packed in a glass column, and deionized water was made to flow until neutral.

Example 24

A resin treated in the same manner as in Example 22 except that the amination conditions were changed as follows, was subjected to tests as a gas adsorbent (amino group-containing weakly basic anion exchange resin) in Example 24. Namely, 140 g of a polymer wet with water, drained by a center (5 minutes) was put in a 1 L four-necked flask, 200 ml of dimethoxymethane was put, and 438 g of a 48% NaOH was put with stirring. Then, 32.7 g of DETA was put. The temperature was raised from room temperature to a bath temperature of 48° C. (internal temperature of 43° C.) over a period of 30 minutes, followed by stirring for 5 hours. After completion, the resin was taken out, and a reaction solution was drawn, followed by batch washing with deionized water. This operation was repeated three times, the resin was packed in a glass column, and deionized water was made to flow until neutral.

Example 25

A resin treated in the same manner as in Example 17 except that the amination conditions were changed as follows, was subjected to tests as a gas adsorbent (amino group-containing weakly basic anion exchange resin) in Example 25. Namely, 100 g of a polymer wet with water, drained by a center (5 minutes) was put in a 1 L four-necked flask, 200 ml of dimethoxymethane was put, and 438 g of a 48% NaOH was put with stirring. Then, 25.5 g of DETA was put. The temperature was raised from room temperature to a bath temperature of 50° C. (internal temperature of 43° C.) over a period of 30 minutes, followed by stirring for 5 hours. After completion, the resin was taken out, and a reaction solution was drawn, followed by batch washing with deionized water. This operation was repeated three times, the resin was packed in a glass column, and deionized water was made to flow until neutral.

Example 26

50 g of "Sepabeads (registered trademark) EC-EP/S" (tradename, a methacrylic polymer having epoxy groups manufactured by Mitsubishi Chemical Corporation) in a wet state was put in a 1 L four-necked flask equipped with an agitating blade and a condenser tube. 350 ml of deionized water and 50 g of DETA were added thereto, and the temperature was raised to 70° C., followed by stirring at 70° C. for 6 hours. After the reaction, the resin was taken out and washed with deionized water. The resin washed with water was returned to the 1 L four-necked flask again, and 500 ml of a 2 N sulfuric acid aqueous solution was added, followed by stirring at 50° C. for 5 hours. After completion, the resin was washed with deionized water on a Buchner funnel. The resin washed with water was packed in a glass column, and 10 BV of deionized water was made to flow. Further, a 2 N sodium hydroxide aqueous solution was made to flow in an amount of 10 times, and deionized water was made to flow again for conversion to OH form ion form, and the obtained resin was subjected to tests as a gas adsorbent (methacrylic weakly basic anion exchange resin) in Example 26.

Example 27

50 g "Sepabeads (registered trademark) FP-EP200" (tradename, a methacrylic polymer having epoxy groups manufactured by Mitsubishi Chemical Corporation) in a wet state was put in a 1 L four-necked flask equipped with an agitating blade and a condenser tube. 350 ml of deionized water and 50 g of diethylenetriamine (DETA, manufactured by Tokyo Chemical Industry Co., Ltd.) were added thereto, and the temperature was raised to 100° C., followed by stirring at 100° C. for 10 hours. After the reaction, the resin was taken out and washed with deionized water. The resin washed with water was returned to the 1 L four-necked flask again, and 500 ml of a 2 N sulfuric acid aqueous solution was added, followed by stirring at 50° C. for 5 hours. After completion, the resin was washed with deionized water on a Buchner funnel. The resin washed with water was packed in a glass column, and 10 BV of deionized water was made to flow. Further, a 2 N sodium hydroxide aqueous solution was made to flow in an amount of 10 times, and deionized water was made to flow again for conversion to OH form ion form, and the obtained resin was subjected to tests as a gas adsorbent (methacrylic weakly basic anion exchange resin) in Example 27.

Example 28

A resin treated in the same manner as in Example 27 except that "Sepabeads (registered trademark) FP-EP300" (tradename, methacrylic polymer having epoxy groups manufactured by Mitsubishi Chemical Corporation) was used instead of "Sepabeads (registered trademark) EC-EP200", was subjected to tests as a gas adsorbent (methacrylic weakly basic anion exchange resin) in Example 28.

Example 29

A resin treated in the same manner as in Example 27 except that "Sepabeads (registered trademark) FP-EC-EP/S" (tradename, methacrylic polymer having epoxy groups manufactured by Mitsubishi Chemical Corporation) was used instead of "Sepabeads (registered trademark) EC-EP200", was subjected to tests as a gas adsorbent (methacrylic weakly basic anion exchange resin) in Example 29.

Example 30

"Sepabeads (registered trademark) FP-HA13" (tradename, methacrylic weakly basic anion exchange resin manufactured by Mitsubishi Chemical Corporation) itself was subjected to tests as a gas adsorbent (methacrylic weakly basic anion exchange resin) in Example 30.

Comparative Example 1

DIAION (registered trademark) CR20 (tradename, amino group-containing weakly basic anion exchange resin manufactured by Mitsubishi Chemical Corporation) itself was subjected to tests as a gas adsorbent (amino group-containing weakly basic anion exchange resin) in Comparative Example 1.

Comparative Example 2

Duolite A7 (tradename, phenolic weakly basic anion exchange resin manufactured by Rohm & Haas) itself was subjected to tests as a gas adsorbent (phenolic weakly basic anion exchange resin) in Comparative Example 2.

Comparative Example 3

400 ml of cyclohexane and 800 mg of ethyl cellulose were put in a 1 L four-necked flask to prepare a polymer bath solution. Separately, a monomer solution comprising 180 g of vinylformamide ($CH_2=CH-NHCHO$) (purity: 94%, main impruty: formic acid), 20.0 g of divinylbenzene (purity: 80%), 4.5 g of deionized water and 400 mg of V-50 (azo polymerization initiator, tradename, manufactured by Wako Pure Chemical Industries, Ltd.) was prepared. Both the solutions were preliminarily bubbled with nitrogen.

While the cyclohexane solution was stirred at 100 rpm in a nitrogen atmosphere, the above-prepared monomer solution was gradually added dropwise. The solution was stirred for 30 minutes until partition equilibrium, the temperature was raised, and polymerization was conducted at 65° C. for 8 hours. After completion of the temperature raise, the monomer phase was gelated in about 15 minutes. After completion of the polymerization, the reaction solution was poured on a Buchner funnel, the obtained crosslinked polymer was washed with methanol to remove remaining divinylbenzene, cyclohexane and the like, and subsequently washed with water. The polymer yield was 81%. The obtained crosslinked copolymer was white in outer appearance but was slightly opaque as observed by a microscope. The obtained polymer was a gel-form crosslinked copolymer having a degree of swelling of 4.63 ml/g and a moisture content of 68.9%, and had a specific surface area of 0 $m^2/g$.

100 ml of the above crosslinked copolymer drained and 100 ml of deionized water were put in a 500 ml flask, and 25 g of sodium hydroxide was added thereto, followed by hydrolysis at 90° C. for 4 hours. After completion of the reaction, the crosslinked copolymer was washed with water, and the obtained copolymer was subjected to tests as a gas adsorbent (gel-form weakly basic anion exchange resin having amino groups) in Comparative Example 3.

The obtained crosslinked copolymer (gas adsorbent) had an average particle size of about 330 μm, a degree of swelling of 7.33 ml/g and a moisture content of 78.9%.

Comparative Example 4

Particulate activated carbon (manufactured by Kishida Chemical Co., Ltd.) was washed ten times with deionized water in a volume of 50 times until the supernatant liquid became transparent and colorless, and the obtained product was subjected to tests as a gas adsorbent (activated carbon) in Comparative Example 4.

Comparative Example 5

Aminated silica gel was prepared by the following method.
In a 1.5 L pressure reaction can, 20.0 g of "Wakogel C-200" (tradename, silica gel manufactured by Wako Pure Chemical Industries, Ltd.), 100 g of toluene and 20.0 g of γ-aminopropyltriethoxysilane were added, followed by stirring at 130° C. for 10 hours for reaction. Then, the silica carrier formed by the above reaction was washed with methanol three times, finally washed with water and vacuum dried. The obtained aminated silica gel was subjected to tests as a gas adsorbent (amino group-containing silica gel) in Comparative Example 5.

Comparative Example 6

DIAION (registered trademark) SA12A (tradename, styrene gel-form strongly basic anion exchange resin manufactured by Mitsubishi Chemical Corporation) itself was subjected to tests as a gas adsorbent (styrene gel-form strongly basic anion exchange resin) in Comparative Example 6.
The gas adsorbent in Comparative Example 6 is a gel-form anion exchange resin and accordingly no pores were confirmed (surface area was 0).

Comparative Example 7

DIAION (registered trademark) DCA11 (tradename, styrene porous weakly basic anion exchange resin manufactured by Mitsubishi Chemical Corporation) itself was subjected to tests as a gas adsorbent (styrene porous weakly basic anion exchange resin) in Comparative Example 7.

Comparative Example 8

DIAION (registered trademark) WA30 (tradename, styrene highly porous weakly basic anion exchange resin manufactured by Mitsubishi Chemical Corporation) itself was subjected to tests as a gas adsorbent (styrene highly porous weakly basic anion exchange resin) in Comparative Example 8.

Comparative Example 9

DIAION (registered trademark) PA312 (tradename, styrene porous weakly basic anion exchange resin manufactured by Mitsubishi Chemical Corporation) itself was subjected to tests as a gas adsorbent (styrene porous weakly basic anion exchange resin) in Comparative Example 8.

Comparative Example 10

A resin treated in the same manner as in Example 26 except that "Sepabeads (registered trademark) FP-EP200" (tradename, methacrylic polymer having epoxy groups manufactured by Mitsubishi Chemical Corporation) was used instead of "Sapabeads (registered trademark) EC-EP/S", was subjected to tests as a gas adsorbent (methacrylic porous weakly basic anion exchange resin) in Comparative Example 10.

Comparative Example 11

A resin treated in the same manner as in Example 26 except that "Sepabeads (registered trademark) FP-EP300" (tradename, methacrylic polymer having epoxy groups manufactured by Mitsubishi Chemical Corporation) was used instead of "Sapabeads (registered trademark) EC-EP/S", was subjected to tests as a gas adsorbent (acrylic porous weakly basic anion exchange resin) in Comparative Example 11.

Comparative Example 12

30 g of "Sepabeads (registered trademark) FP-EP200" (tradename, methacrylic polymer having epoxy groups manufactured by Mitsubishi Chemical Corporation) in a wet state as a resin was added to a 1 L four-necked flask equipped with an agitating blade and a condenser tube. 350 ml of deionized water and 50 g of DETA were added thereto, and the temperature was raised to 30° C., followed by stirring at 30° C. for 5 hours. After the reaction, the resin was taken out and washed with deionized water. The resin washed with water was returned to the 1 L four-necked flask again, and 500 ml of a 2 N sulfuric acid aqueous solution was added, followed by stirring at 50° C. for 5 hours. After completion, the resin was washed with deionized water on a Buchner funnel. Further, the resin was packed in a glass column and 10 BV of deionized water was made to flow. Further, a 2 N sodium hydroxide aqueous solution was made to flow in an amount of 10 times, and deionized water was made to flow again for conversion to OH form ion form, and the obtained resin was subjected to tests as a gas adsorbent (amino group-containing methacrylic weakly basic anion exchange resin) in Comparative Example 12.

Comparative Example 13

A resin treated in the same manner as in Comparative Example 12 except that "Sepabeads (registered trademark) FP-EP300 (tradename, methacrylic polymer having epoxy groups manufactured by Mitsubishi Chemical Corporation) was used instead of "Sepabeads (registered trademark) EC-EP200", was subjected to tests as a gas adsorbent (methacrylic porous weakly basic anion exchange resin) in Comparative Example 13.

Comparative Example 14

"Sepabeads (registered trademark) FP-HA20" (tradename, acrylic porous weakly basic anion exchange resin manufactured by Mitsubishi Chemical Corporation) itself was subjected to tests as a gas adsorbent (methacrylic weakly basic anion exchange resin having hexamethylenediamino groups) in Comparative Example 14.

Comparative Example 15

"Sepabeads (registered trademark) FP-DA05" (tradename, acrylic porous weakly basic anion exchange resin manufactured by Mitsubishi Chemical Corporation) itself was subjected to tests as a gas adsorbent (methacrylic weakly basic anion exchange resin having dimethylamino groups) in Comparative Example 15.

Comparative Example 16

"Sepabeads (registered trademark) FP-DA20" (tradename, acrylic porous weakly basic anion exchange resin manufactured by Mitsubishi Chemical Corporation) itself was subjected to tests as a gas adsorbent (methacrylic weakly basic anion exchange resin having dimethylamino groups) in Comparative Example 16.

Comparative Example 17

"Sepabeads (registered trademark) FP-HA05" (tradename, acrylic porous weakly basic anion exchange resin manufactured by Mitsubishi Chemical Corporation) itself was subjected to tests as a gas adsorbent (methacrylic weakly basic anion exchange resin having hexamethylenediamino groups) in Comparative Example 17.

Comparative Example 18

"Hokuetsu HS" (tradename, phenolic porous weakly basic anion exchange resin manufactured by Ajinomoto Fine-Techno Co., Inc.) itself was subjected to tests as a gas adsorbent (phenolic porous weakly basic anion exchange resin) in Comparative Example 18.

Comparative Example 19

"Hokuetsu KS" (tradename, phenolic porous weakly basic anion exchange resin manufactured by Ajinomoto Fine-Techno Co., Inc.) itself was subjected to tests as a gas adsorbent (phenolic porous weakly basic anion exchange resin) in Comparative Example 19.

Comparative Example 20

To a 2 L four-necked flask equipped with an agitating blade and a condenser tube, 57.6 g (containing 0.14 mol as the amine) of "Hokuetsu HS" (tradename, phenolic porous weakly basic anion exchange resin manufactured by Ajinomoto Fine-Techno Co., Inc.) vacuum dried at 50° C. until the previous day as a resin was charged. 200 ml (2.59 mol) of chloromethyl methyl ether (CME, manufactured by Wako Pure Chemical Industries, Ltd.) was added thereto, followed by stirring at 25° C. for 0.5 hour. Further, $FeCl_3$ (0.09 g/g resin, 15 g (31 mmol) was added, and the temperature was raised to 45° C., followed by stirring for 8 hours. The reaction was continued in a moderate reflux state. After completion, the flask was cooled to 25° C., and 100 g of deionized water was charged for chloromethylation by hydrolysis.

50 g of the above chloromethylated polymer in a drained state is put in a 500 ml four-necked flask, and 50 ml of DETA is added, followed by stirring at 110° C. The solution gradually becomes a brown solution from a transparent solution. The resin is originally black as activated carbon, but the black state is unchanged. Stirring was carried out at 110° C. for 6 hours. After completion, the resin was washed with water. The obtained resin was subjected to tests as a gas adsorbent (amino group-containing phenolic porous weakly basic anion exchange resin) in Comparative Example 20.

Comparative Example 21

To a 2 L four-necked flask equipped with an agitating blade and a condenser tube, 59.0 g (containing 0.14 mol as the amine) of "Hokuetsu KS" (tradename, phenolic porous weakly basic anion exchange resin manufactured by Ajinomoto Fine-Techno Co., Inc.) vacuum dried at 50° C. was charged. 200 ml (2.59 mol) of CME was added thereto, followed by stirring at 25° C. for 0.5 hour. Further, $FeCl_3$ (0.17 g/g resin, 15 g (62 mmol) was added, and the temperature was raised to 45° C., followed by stirring for 8 hours. The reaction was continued in a moderate reflux state. After completion, the flask was cooled to 25° C., and 100 g of deionized water was charged for chloromethylation by hydrolysis.

The above obtained chloromethylated polymer was aminated in the same manner as in Comparative Example 20, and the obtained resin was subjected to tests as a gas adsorbent (amino group-containing phenolic porous weakly basic anion exchange resin) in Comparative Example 21.

Comparative Example 22

"Hokuetsu HS" (phenolic porous weakly basic anion exchange resin manufactured by Ajinomoto Fine-Techno Co., Inc.) as a resin was chloromethylated in the same manner as in Comparative Example 20.

50 g of the above chloromethylated polymer in a drained state was put in a 500 ml four-necked flask, and 60 ml of ethylenediamine (EDA) was added, followed by stirring at 100° C. The solution gradually becomes a brown solution from a transparent solution. The resin is originally black as activated carbon, but the black state is unchanged. Stirring was carried out at 100° C. for 6 hours. After completion, the resin was washed with water. A 2 N hydrochloric acid was made to flow through the resin washed with water, whereupon a reddish brown solution was effused. The solution was gradually changed to yellow, pale yellow and then colorless. The resin was further washed with 10 BV of deionized water, 10 BV of a 2 N NaOH aqueous solution was made to flow, and the resin was washed with 20 BV of deionized water again, and the obtained resin was subjected to tests as a gas adsorbent (amino group-containing phenolic porous weakly basic anion exchange resin) in Comparative Example 20.

Comparative Example 23

"Hokuetsu KS" (phenolic porous weakly basic anion exchange resin manufactured by Ajinomoto Fine-Techno Co., Inc.) as a resin was chloromethylated in the same manner as in Comparative Example 21.

The above obtained chloromethylated polymer was aminated in the same manner as in Comparative Example 22, and the obtained resin was subjected to tests as a gas adsorbent (amino group-containing phenolic porous weakly basic anion exchange resin) in Comparative Example 23.

Comparative Example 24

To 50.0 g of silica gel (Micro Bead Silica Gel Grade 500-75/200 Lot No 4012796, manufactured by FUJI SILYSIA CHEMICAL LTD.), 150 ml of toluene (JUNSEI CHEMICAL CO., LTD.) dried over molecular sieves 4A (manufactured by Kishida Chemical Co., Ltd.) and 50.0 g (0.226 mol) of 3-aminopropyltriethoxysilane (manufactured by Tokyo Chemical Industry Co., Ltd.) were added, and the bath temperature was set at 110° C. (internal temperature: 108° C.), followed by stirring for 8 hours. When the solution was mixed, it was a transparent suspended solution, but after a lapse of one hour, the solution gradually became a milky white suspended solution. After the reaction, the silica gel was washed with toluene and further washed with methanol, and further washed with deionized water. The obtained silica gel was vacuum dried at 50° C. for 10 hours, and the obtained resin was subjected to tests as a gas adsorbent (silica gel weakly basic anion exchange resin) in Comparative Example 24.

The dried silica gel was subjected to elemental analysis to measure the N content, and the acid adsorption amount was measured.

Comparative Example 25

To 50.0 g of silica gel (Micro Bead Silica Gel Grade 1000-75/200 Lot No 2080990, manufactured by FUJI SILYSIA CHEMICAL LTD.), 150 ml of toluene (JUNSEI CHEMICAL CO., LTD.) dried over molecular sieves 4A (manufactured by JUNSEI CHEMICAL CO., LTD., special grade) and 50.0 g (0.226 mol) of 3-aminopropyltriethoxysilane (manufactured by Tokyo Chemical Industry Co., Ltd.) were added, and the bath temperature was set at 110° C. (internal temperature: 108° C.), followed by stirring for 8 hours. When the solution was mixed, it was a transparent suspended solution, but after a lapse of one hour, the solution gradually became a milky white suspended solution. After the reaction, the silica gel was washed with toluene and further washed with ethanol, and further washed with deionized water.

The obtained silica gel was vacuum dried at 5° C. for 10 hours, and the obtained resin was subjected to tests as a gas adsorbent (silica gel weakly basic anion exchange resin) in Comparative Example 25.

The dried silica gel was subjected to elemental analysis to measure the N content, and the acid adsorption amount was measured.

Comparative Example 26

To 50.0 g of silica gel (Micro Bead Silica Gel Grade 2000-75/200 Lot No 3121290, manufactured by FUJI SILYSIA CHEMICAL LTD.), 150 ml of toluene dried over molecular sieves 4A (manufactured by JUNSEI CHEMICAL CO., LTD., special grade) and 50.0 g (0.226 mol) of 3-aminopropyltriethoxysilane (manufactured by Tokyo Chemical Industry Co., Ltd.) were added, and the bath temperature was set at 110° C. (internal temperature: 108° C.), followed by stirring for 8 hours. The solution was in a slight reflux state. When the solution was mixed, it was a transparent suspended solution, but after a lapse of one hour, the solution gradually became a milky white suspended solution. After the reaction, the silica gel was washed with toluene and further washed with ethanol, and further washed with deionized water. The obtained silica gel was vacuum dried at 50° C. for 10 hours, and the obtained resin was subjected to tests as a gas adsorbent (silica gel weakly basic anion exchange resin) in Comparative Example 26. The dried silica gel was subjected to elemental analysis to measure the N content, and the acid adsorption amount was measured.

Comparative Example 27

30.0 g of silica gel (Micro Bead Silica Gel Grade 500-75/200 Lot No 4012796, manufactured by FUJI SILYSIA CHEMICAL LTD.), 50 ml of ethanol (JUNSEI CHEMICAL CO., LTD., special grade), 50 ml of deionized water and 30.0 g (0.226 mol) of 3-aminopropyltriethoxysilane (manufactured by Tokyo Chemical Industry Co., Ltd.) were added, and the bath temperature was set at 80° C. (internal temperature: 108° C.), followed by stirring for 8 hours. When the solution was mixed, it was a transparent suspended solution, but after a lapse of one hour, the solution gradually became a milky white suspended solution.

After the reaction, the silica gel was washed with ethanol and further washed with methanol, and further washed with deionized water. The obtained silica gel was vacuum dried at 50° C. for 10 hours, and the obtained resin was subjected to tests as a gas adsorbent (silica gel weakly basic anion exchange resin) in Comparative Example 27. The dried silica gel was subjected to elemental analysis to measure the N content, and the acid adsorption amount was measured.

Comparative Example 28

30.0 g of silica gel (Micro Bead Silica Gel Grade 2000-75/200 Lot No 3121290, manufactured by FUJI SILYSIA CHEMICAL LTD.), 50 ml of ethanol, 50 ml of deionized water and 30.0 g (0.226 mol) of 3-aminopropyltriethoxysilane (manufactured by Tokyo Chemical Industry Co., Ltd.) were added, and the bath temperature was set at 80° C. (internal temperature: 78° C.) followed by stirring for 8 hours. The solution was slightly refluxed.

When the solution was mixed, it was a transparent suspended solution, but after a lapse of one hour, the solution gradually became a milky white suspended solution.

After the reaction, the silica gel carrier was washed with ethanol and further washed with methanol, and further washed with deionized water.

The obtained silica gel was vacuum dried at 50° C. for is 10 hours, and the obtained resin was subjected to tests as a gas adsorbent (silica gel weakly basic anion exchange resin) in Comparative Example 28.

The dried silica gel was subjected to elemental analysis to measure the N content, and the acid adsorption amount was measured.

Comparative Example 29

35.0 g of silica gel (Micro Bead Silica Gel Grade 500-75/200 Lot No 4012796, manufactured by FUJI SILYSIA CHEMICAL LTD.), 100 ml of tetrahydrofuran (THF) (manufactued by JUNSEI CHEMICAL CO., LTD., special grade) and 35.0 g (0.226 mol) of 3-aminopropyltriethoxysilane (manufactured by Tokyo Chemical Industry Co., Ltd.) were added, and the bath temperature was set at 70° C. (internal temperature: 67° C.), followed by stirring for 8 hours. The solution was a transparent suspended solution from the beginning. After the reaction, the silica gel was washed with THF and further washed with methanol, and further washed with deionized water. The obtained silica gel was vacuum dried at 50° C. for 10 hours, and the obtained resin was subjected to tests as a gas adsorbent (silica gel weakly basic anion exchange resin) in Comparative Example 29.

The dried silica gel was subjected to elemental analysis to measure the N content.

Comparative Example 30

35.0 g of silica gel (Micro Bead Silica Gel Grade 2000-75/200 Lot No 3121290, manufactured by FUJI SILYSIA CHEMICAL LTD.), 100 ml of THF and 35.0 g (0.226 mol) of 3-aminopropyltriethoxysilane were added, and the bath temperature was set at 70° C. (internal temperature: 67° C.) followed by stirring for 8 hours. The solution was a transparent suspended solution from the beginning. After the reaction, the silica gel was washed with THF and further washed with methanol, and further washed with deionized water. The obtained silica gel was vacuum dried at 50° C. for 10 hours, and the obtained resin was subjected to tests as a gas adsorbent (silica gel weakly basic anion exchange resin) in Comparative Example 30. The dried silica gel was subjected to elemental analysis to measure the N content.

Comparative Example 31

35.0 g of silica gel (Merck Silica Gel 60 1,07734,1000, manufactured by Merck), 100 ml of THF and 35.0 g (0.226 mol) of 3-aminopropyltriethoxysilane were added, and the bath temperature was set at 70° C. (internal temperature: 67° C.), followed by stirring for 8 hours. The solution was a transparent suspended solution from the beginning. After the reaction, the silica gel was washed with THF and further washed with methanol, and further washed with deionized water. The obtained silica gel was vacuum dried at 50° C. for 5 hours, and the obtained resin was subjected to tests as a gas adsorbent (silica gel weakly basic anion exchange resin) in Comparative Example 31. The dried silica gel was subjected to elemental analysis to measure the N content.

Comparative Example 32

50.0 g of silica gel (Micro Bead Silica Gel Grade 500-75/200 Lot No 4012796, manufactured by FUJI SILYSIA CHEMICAL LTD.), 50 ml of toluene dried over molecular sieves 4A (manufactured by JUNSEI CHEMICAL CO., LTD., special grade) and 35.0 g (0.132 mol) of 3(2(2-aminomethylamino)ethylamino)propyl-trimethoxysilane (manufactured by Sigma-Aldrich) were added, and the bath temperature was set at 110° C. (internal temperature: 108° C.), followed by stirring for 8 hours. The solution was a transparent suspended solution from the beginning. After the reaction, the silica gel was washed with toluene and further washed with methanol, and further washed with deionized water. The obtained silica gel was vacuum dried at 50° C. for 10 hours, and the obtained resin was subjected to tests as a gas adsorbent (silica gel weakly basic anion exchange resin) in Comparative Example 32. The dried silica gel was subjected to elemental analysis to measure the N content.

Comparative Example 33

50.0 g of silica gel (Micro Bead Silica Gel Grade 2000-75/200 Lot No 3121290, manufactured by FUJI SILYSIA CHEMICAL LTD.), 50 ml of toluene dried over molecular sieves 4A (manufactured by JUNSEI CHEMICAL CO., LTD., special grade) and 35.0 g (0.132 mol) of 3(2(2-aminomethylamino)ethylamino)propyl-trimethoxysilane (manufactured by Sigma-Aldrich) were added, and the bath temperature was set at 70° C. (internal temperature: 68° C.), followed by stirring for 8 hours. The solution was a transparent suspended for a porous material, although it was slightly opaque. After the reaction, the silica gel was washed with toluene and further washed with methanol, and further washed with deionized water. The obtained silica gel was vacuum dried at 50° C. for 10 hours, and the obtained resin was subjected to tests as a gas adsorbent (silica gel weakly basic anion exchange resin) in Comparative Example 33. The dried silica gel was subjected to elemental analysis to measure the N content.

Comparative Example 34

35.0 g of silica gel (Wako-gel C-300, manufactured by Wako Pure Chemical Industries, Ltd.), 50 ml of toluene dried over molecular sieves 4A (manufactured by JUNSEI CHEMICAL CO., LTD., special grade) and 50.0 g of 3(2(2-aminomethylamino)ethylamino)propyl-trimethoxysilane (manufactured by Sigma-Aldrich) were added, and the bath temperature was set at 70° C. (internal temperature: 68° C.), followed by stirring for 8 hours.

The solution was a transparent suspended solution from the beginning. After the reaction, the silica gel was washed with toluene and further washed with methanol, and further washed with deionized water. The obtained silica gel was vacuum dried at 50° C. for 5 hours, and the obtained resin was subjected to tests as a gas adsorbent (silica gel weakly basic anion exchange resin) in Comparative Example 34. The dried silica gel was subjected to elemental analysis to measure the N content.

The gas adsorbents obtained in Examples and Comparative Examples were evaluated by the above respective tests. The results are shown in Tables 1 to 4.

TABLE 1

| | Moisture content (%) | Mean pore radius (Å) | Pore volume (ml/g) | Surface area (m²/g) | Amine elution amount (μeq/g) | Monocyclic aromatic compound content (μg/g) | Neutral salt decomposition capacity (meq/g) | Acid adsorption capacity | |
|---|---|---|---|---|---|---|---|---|---|
| | | | | | | | | meq/g | meq/mL |
| Ex. 1 | 57.1 | 600 | 0.84 | 50 | 0.08 | 0.2 | 0.42 | 3.67 | 1.06 |
| Ex. 2 | 55.1 | 550 | 0.78 | 55 | 0.07 | 0.3 | 0.14 | 3.16 | 0.86 |
| Ex. 3 | 56.5 | 650 | 0.86 | 45 | 0.08 | 0.5 | 0.31 | 4.53 | 1.44 |
| Ex. 4 | 53.6 | 605 | 0.83 | 50 | <0.1 | <0.1 | 0.14 | 4.89 | 1.52 |
| Ex. 5 | 53.1 | 595 | 0.84 | 52 | <0.1 | <0.1 | 0.12 | 4.42 | 1.39 |
| Ex. 6 | 52.1 | 590 | 0.81 | 51 | <0.1 | <0.1 | 0.09 | 3.78 | 1.22 |
| Ex. 7 | 57.1 | 600 | 0.84 | 50 | <0.1 | <0.1 | 0.42 | 3.67 | 1.06 |
| Ex. 8 | 57.1 | 600 | 0.84 | 50 | <0.1 | <0.1 | 0.42 | 3.67 | 1.06 |
| Ex. 9 | 57.1 | 600 | 0.84 | 50 | <0.1 | <0.1 | 0.42 | 3.67 | 1.06 |
| Ex. 10 | 61.5 | 1,410 | 1.38 | 27 | <0.1 | <0.1 | 0.08 | 2.59 | 0.67 |
| Ex. 11 | 54.5 | 510 | 0.80 | 68 | <0.1 | <0.1 | 0.13 | 4.36 | 1.36 |
| Ex. 12 | 56.7 | 605 | 0.84 | 48 | <0.1 | <0.1 | 0.11 | 4.10 | 1.2 |

TABLE 1-continued

|  | Propionaldehyde adsorption amount (mg/g) | Propionaldehyde aqueous solution concentration (ppm) | | Gaseous phase system gas capturing performance | Nicotinamide adsorption amount (mg/g) | 1-menthol adsorption amount (mg/g) | Number average particle size (μm) |
|---|---|---|---|---|---|---|---|
|  |  | After 3 minutes | After 10 minutes |  |  |  |  |
| Ex. 1 | 358 | 58 | 28 | — | 0.0 | 23 | 550 |
| Ex. 2 | 373 | — | 3.6 | — | 0.0 | 20 | 550 |
| Ex. 3 | 345 | — | 10.6 | — | 0.0 | 27 | 550 |
| Ex. 4 | — | 27.7 | — | — | 0.0 | 21 | 550 |
| Ex. 5 | — | 37 | — | — | 0.0 | 19 | 550 |
| Ex. 6 | — | 46 | — | — | 0.0 | 15 | 550 |
| Ex. 7 | — | 58 | — | — | — | — | 510 |
| Ex. 8 | — | 66 | — | — | — | — | 700 |
| Ex. 9 | — | 51 | — | — | — | — | 350 |
| Ex. 10 | — | 45 | — | — | — | — | 550 |
| Ex. 11 | — | 29 | — | — | — | — | 550 |
| Ex. 12 | — | 41 | — | — | — | — | 550 |

* In table 1, moisture content (%) represents moisture content of the gas adsorbent in a drained state.
* In Table 1, "—" represents no data.

TABLE 2

|  | Moisture content (%) | Mean pore radius (Å) | Pore volume (ml/g) | Surface area (m²/g) | Amine elution amount (μeq/g) | Monocyclic aromatic compound content (μg/g) | Neutral salt decomposition capacity (meq/g) | Acid adsorption capacity | |
|---|---|---|---|---|---|---|---|---|---|
|  |  |  |  |  |  |  |  | meq/g | meq/mL |
| EX. 13 | 52.8 | 750 | 0.916 | 56 | <0.1 | — | 0.09 | 3.94 | 1.24 |
| EX. 14 | 52.6 | 754 | 0.889 | 51 | <0.1 | — | 0.08 | 3.92 | 1.24 |
| EX. 15 | 52.2 | 754 | 0.923 | 48 | <0.1 | — | 0.07 | 3.52 | 1.12 |
| EX. 16 | 51.6 | 752 | 0.913 | 52 | <0.1 | — | 0.06 | 2.83 | 0.92 |
| EX. 17 | 57.9 | 752 | 1.31 | 40 | <0.1 | — | 0.06 | 2.75 | 0.76 |
| EX. 18 | 59.2 | 889 | 1.24 | 33 | <0.1 | — | 0.04 | 2.97 | 0.80 |
| EX. 19 | 61.5 | 1,410 | 1.38 | 27 | <0.1 | — | 0.08 | 2.59 | 0.67 |
| EX. 20 | 56.7 | 390 | 0.65 | 39 | <0.1 | — | 0.09 | 5.51 | 1.59 |
| EX. 21 | 57.1 | 400 | 0.78 | 41 | <0.1 | — | 0.10 | 4.99 | 1.46 |
| EX. 22 | 55.2 | 600 | 1.08 | 67 | <0.1 | — | 0.09 | 4.84 | 1.51 |
| EX. 23 | 52.5 | 749 | 0.95 | 48 | <0.1 | — | 0.07 | 3.37 | 1.04 |
| EX. 24 | 57.1 | 600 | 0.96 | 54 | <0.1 | — | 0.1 | 5.06 | 1.53 |
| EX. 25 | 57.8 | 747 | 1.28 | 45 | <0.1 | — | 0.06 | 2.97 | 0.82 |
| EX. 26 | 59.8 | 390 | 0.77 | 160 | <0.1 | — | 0.04 | 2.6 | 0.62 |
| EX. 27 | 60.4 | 370 | 0.21 | 37 | <0.1 | — | 0.08 | 2.61 | 0.62 |
| EX. 28 | 65.2 | 380 | 0.13 | 24 | <0.1 | — | 0.1 | 2.54 | 0.5 |
| EX. 29 | 60.3 | 400 | 0.56 | 104 | <0.1 | — | 0.07 | 3.05 | 0.82 |
| EX. 30 | 54.0 | 420 | 0.42 | 53 | <0.1 | — | 0.03 | 2.28 | 0.74 |

|  | Propionaldehyde adsorption amount (mg/g) | Propionaldehyde aqueous solution concentration (ppm) | | Gaseous phase system gas capturing performance | Nicotinamide adsorption amount (mg/g) | 1-menthol adsorption amount (mg/g) | Number average particle size (μm) |
|---|---|---|---|---|---|---|---|
|  |  | After 3 minutes | After 10 minutes |  |  |  |  |
| EX. 13 | — | 36 | — | 81 | — | — | 550 |
| EX. 14 | — | 36 | — | 83 | — | — | 550 |
| EX. 15 | — | 35 | — | 82 | — | — | 550 |
| EX. 16 | — | 38 | — | 81 | — | — | 550 |
| EX. 17 | — | 64 | — | 78 | — | — | 550 |
| EX. 18 | — | 67 | — | 76 | — | — | 550 |
| EX. 19 | — | 55 | — | — | — | — | 550 |
| EX. 20 | — | 45 | — | — | — | — | 550 |
| EX. 21 | — | 44 | — | — | — | — | 550 |
| EX. 22 | — | 58 | — | — | — | — | 550 |
| EX. 23 | — | 42 | — | 84 | — | — | 550 |
| EX. 24 | — | 53 | — | — | — | — | 550 |
| EX. 25 | — | 61 | — | 78 | — | — | 550 |
| EX. 26 | — | 47 | — | — | — | — | 150 |
| EX. 27 | — | 52 | — | 47 | — | — | 150 |
| EX. 28 | — | 64 | — | — | — | — | 150 |
| EX. 29 | — | 35 | — | 95 | — | — | 150 |
| EX. 30 | — | 59 | — | — | — | — | 150 |

* In table 1, moisture content (%) represents moisture content of the gas adsorbent in a drained state.
* In Table 1, "—" represents no data.

TABLE 3

| | Moisture content | Mean pore radius | Pore volume | Surface area | Amine elution amount | Monocyclic aromatic compound content | Neutral salt decomposition capacity | Acid adsorption capacity | |
|---|---|---|---|---|---|---|---|---|---|
| | (%) | (Å) | (ml/g) | (m²/g) | (µeq/g) | (µg/g) | (meq/g) | meq/g | meq/mL |
| Comp. EX. 1 | 56.7 | 600 | 0.84 | 50 | 18 | 4,800 | 0.45 | 3.65 | 1.04 |
| Comp. EX. 2 | 56.3 | 200 | 0.93 | 120 | 6 | 6.5 | 0.02 | 2.2 | 0.67 |
| Comp. EX. 3 | 78.9 | 0 | 18 | 0 | 12 | 800 | 0.05 | 18 | 2.45 |
| Comp. EX. 4 | 34 | 19 | 0.22 | 490 | 0 | 15 | 0.01 | 1.2 | 0.43 |
| Comp. EX. 5 | 48 | 150 | 0.9 | 200 | 0.8 | 0.5 | 0.01 | 1.8 | 0.78 |
| Comp. EX. 6 | 52.1 | 0 | 0 | 0 | 1.8 | — | 4.28 | 4.28 | — |
| Comp. EX. 7 | 58.5 | 260 | 0.67 | 670 | 3 | — | 0.1 | 1.58 | 0.42 |
| Comp. EX. 8 | 51.1 | 340 | 0.37 | 23 | 3.6 | 2,100 | 0.62 | 5.16 | 1.06 |
| Comp. EX. 9 | 54.5 | 0 | 0 | 0 | 3 | — | 3.96 | 3.96 | 0.35 |
| Comp. EX. 10 | 59.0 | 270 | 0.23 | 45 | <0.1 | — | 0.04 | 1.59 | 0.395 |
| Comp. EX. 11 | 65.2 | 280 | 0.15 | 27 | <0.1 | — | 0.05 | 1.46 | 0.275 |
| Comp. EX. 12 | 57.8 | 230 | 0.22 | 48 | <0.1 | — | 0.04 | 1.02 | 0.26 |
| Comp. EX. 13 | 64.2 | 250 | 0.16 | 30 | <0.1 | — | 0.05 | 0.92 | 0.18 |
| Comp. EX. 14 | 39.4 | 136 | 0.39 | 64 | <0.1 | — | 0.02 | 1.88 | 0.89 |
| Comp. EX. 15 | 66.9 | 3,195 | 1.75 | 19 | <0.1 | — | 0.04 | 2.39 | 0.53 |
| Comp. EX. 16 | 40.7 | 132 | 0.33 | 46 | <0.1 | — | 0.02 | 1.88 | 0.84 |
| Comp. EX. 17 | 67.6 | 3,500 | 1.65 | 20 | <0.1 | — | 0.05 | 1.65 | 0.36 |

| | Propionaldehyde adsorption amount (mg/g) | Propionaldehyde aqueous solution concentration (ppm) | | Gaseous phase system gas capturing performance | Nicotinamide adsorption amount (mg/g) | 1-menthol adsorption amount (mg/g) | Number average particle size (µm) |
|---|---|---|---|---|---|---|---|
| | | After 3 minutes | After 10 minutes | | | | |
| Comp. EX. 1 | 221 | 61 | — | — | 0.0 | 25 | 550 |
| Comp. EX. 2 | 130 | 86 | — | 30 | 0.0 | 15 | 650 |
| Comp. EX. 3 | 340 | 89 | — | — | 0.0 | 18 | 500 |
| Comp. EX. 4 | 321 | 82 | — | — | 15.0 | 73 | 1,000 |
| Comp. EX. 5 | 180 | 85 | — | — | 0.0 | 18 | 150 |
| Comp. EX. 6 | — | — | 94 | — | — | — | 700 |
| Comp. EX. 7 | — | — | 93 | — | — | — | — |
| Comp. EX. 8 | — | — | 84 | 78 | — | — | 700 |
| Comp. EX. 9 | — | — | 84 | — | — | — | 700 |
| Comp. EX. 10 | — | — | 76 | — | — | — | 150 |
| Comp. EX. 11 | — | — | 73 | — | — | — | 150 |
| Comp. EX. 12 | — | — | 86 | — | — | — | 150 |
| Comp. EX. 13 | — | — | 83 | — | — | — | 150 |
| Comp. EX. 14 | — | — | 77 | — | — | — | 150 |
| Comp. EX. 15 | — | — | 91 | — | — | — | 150 |
| Comp. EX. 16 | — | — | 90 | — | — | — | 150 |
| Comp. EX. 17 | — | — | 89 | — | — | — | 150 |

\* In table 1, moisture content (%) represents moisture content of the gas adsorbent in a drained state.
\* In Table 1, "—" represents no data.

TABLE 4

| | Moisture content | Mean pore radius | Pore volume | Surface area | Amine elution amount | Monocyclic aromatic compound content | Neutral salt decomposition capacity | Acid adsorption capacity | |
|---|---|---|---|---|---|---|---|---|---|
| | (%) | (Å) | (ml/g) | (m²/g) | (µeq/g) | (µg/g) | (meq/g) | meq/g | meq/mL |
| Comp. EX. 18 | 71.5 | 18 | 0.25 | 523 | 0.3 | — | 0.1 | 2.41 | 0.5 |
| Comp. EX. 19 | 71.9 | 0 | 0 | 0 | 0.2 | — | 0.12 | 2.74 | 0.47 |
| Comp. EX. 20 | 57.3 | 47 | 0.35 | 270 | 0.4 | — | 0.16 | 3.97 | 1.26 |
| Comp. EX. 21 | 51.4 | 23 | 0.1 | 430 | 0.4 | — | 0.14 | 3.41 | 1.26 |
| Comp. EX. 22 | 59.3 | 68 | 0.32 | 250 | 0.2 | — | 0.23 | 3.89 | 1.18 |
| Comp. EX. 23 | 56.0 | 13 | 0.13 | 450 | 0.3 | — | 0.15 | 3.68 | 1.2 |
| Comp. EX. 24 | 47.5 | 226 | 0.79 | 44 | <0.1 | — | 0.02 | 0.37 | — |
| Comp. EX. 25 | 47.1 | 390 | 0.8 | 27 | <0.1 | — | 0.02 | 0.27 | — |
| Comp. EX. 26 | 47.2 | 749 | 0.83 | 13 | <0.1 | — | 0.01 | 0.14 | — |
| Comp. EX. 27 | 47.9 | 228 | 0.81 | 46 | <0.1 | — | 0.02 | 0.26 | — |
| Comp. EX. 28 | 47.5 | 749 | 0.843 | 14 | <0.1 | — | 0.01 | 0.08 | — |
| Comp. EX. 29 | 47.5 | 225 | 0.799 | 47 | <0.1 | — | 0.02 | 0.20 | — |
| Comp. EX. 30 | 47.5 | 744 | 0.828 | 16 | <0.1 | — | 0.01 | 0.08 | — |
| Comp. EX. 31 | 47.9 | 26 | 0.54 | 313 | <0.1 | — | 0.13 | 1.60 | — |
| Comp. EX. 32 | 39.0 | 226 | 0.765 | 40 | <0.1 | — | 0.11 | 0.22 | — |

TABLE 4-continued

| | | | | | | | | | |
|---|---|---|---|---|---|---|---|---|---|
| Comp. EX. 33 | — | 745 | 0.817 | 12 | <0.1 | — | 0.01 | 0.07 | — |
| Comp. EX. 34 | — | 25.5 | 0.55 | 240 | <0.1 | — | 0.06 | 0.75 | — |

| | Propionaldehyde adsorption amount (mg/g) | Propionaldehyde aqueous solution concentration (ppm) | | Gaseous phase system gas capturing performance | Nicotinamide adsorption amount (mg/g) | 1-menthol adsorption amount (mg/g) | Number average particle size (μm) |
|---|---|---|---|---|---|---|---|
| | | After 3 minutes | After 10 minutes | | | | |
| Comp. EX. 18 | — | 85 | — | 35 | — | — | 400 |
| Comp. EX. 19 | — | 87 | — | — | — | — | 450 |
| Comp. EX. 20 | — | 72 | — | — | — | — | 400 |
| Comp. EX. 21 | — | 75 | — | — | — | — | 450 |
| Comp. EX. 22 | — | 73 | — | — | — | — | 400 |
| Comp. EX. 23 | — | 74 | — | 30 | — | — | 450 |
| Comp. EX. 24 | — | 71 | — | — | — | — | 150 |
| Comp. EX. 25 | — | 95 | — | — | — | — | 150 |
| Comp. EX. 26 | — | 95 | — | 5 | — | — | 150 |
| Comp. EX. 27 | — | 83 | — | — | — | — | 150 |
| Comp. EX. 28 | — | 92 | — | — | — | — | 150 |
| Comp. EX. 29 | — | 85 | — | — | — | — | 150 |
| Comp. EX. 30 | — | 93 | — | — | — | — | 150 |
| Comp. EX. 31 | — | 96 | — | — | — | — | 150 |
| Comp. EX. 32 | — | 76 | — | — | — | — | 150 |
| Comp. EX. 33 | — | 90 | — | 8 | — | — | 150 |
| Comp. EX. 34 | — | 100 | — | 39 | — | — | 150 |

* In table 1, moisture content (%) represents moisture content of the gas adsorbent in a drained state.
* In Table 1, "—" represents no data.

INDUSTRIAL APPLICABILITY

The gas adsorbent of the present invention can be used in a wide range of fields, such as a cigarette filter and a gas filter of apparatus to remove noxious gas in cigarette smoke such as an air cleaner or a car air conditioner, and removal of noxious gas contained in building material, odor emitted in the cooking place, a filter for a muffler for an automobile, a deodorant in a bath room, or removal of noxious gas and odor components in a sewage plant, a waste incineration plant, a garbage truck, a waste truck, a collection cabinet, an air conditioner, a refrigerator, the furniture, a cushion, a stuffed toy, disposal diapers, a sewerage pipe or sewerage works.

The entire disclosures of Japanese Patent Application No. 2005-232625 filed on Aug. 10, 2005, Japanese Patent Application No. 2005-232648 filed on Aug. 10, 2005, Japanese Patent Application No. 2005-232655 filed on Aug. 10, 2005, Japanese Patent Application No. 2005-298214 filed on Oct. 12, 2005 and Japanese Patent Application No. 2006-213977 filed on Aug. 4, 2006 including specifications, claims, drawings and summaries are incorporated herein by reference in their entireties.

The invention claimed is:

1. A gas adsorbent capable of adsorbing gas in a cigarette filter wherein the gas absorbent satisfies the following conditions (I), (II), (IV) and (V):
   (I) the mean pore radius of the gas adsorbent is at least 330 Å and at most 3,000 Å as measured by a mercury porosimeter;
   (II) the amine elution amount from the gas adsorbent per unit mass is at most 10 μeq/g;
   (IV) the neutral salt decomposition capacity of the gas absorbent is at most 0.43 meq/g; and
   (V) the acid adsorption capacity of the gas adsorbent per unit mass is at least 1.5 meq/g;
   wherein the gas adsorbent is a weakly basic anion exchange resin having amino groups which has been washed with a strong acid.

2. The gas adsorbent according to claim 1, wherein the weakly basic anion exchange resin is obtained by introducing ion exchange groups to a crosslinked polystyrene.

3. The gas adsorbent according to claim 2, wherein the crosslinked polystyrene is obtained by a high temperature polymerization reaction.

4. The gas adsorbent according to claim 2, wherein the crosslinked polystyrene is a styrene/divinylbenzene resin.

5. The gas adsorbent according to claim 3, wherein the polymerization temperature in the high temperature polymerization reaction is at least 100° C. and at most 160° C.

6. The gas adsorbent according to claim 1, wherein the strong acid is a 0.1 to 5 N acid selected from the group consisting of hydrochloric acid, sulfuric acid, phosphoric acid, acetic acid and nitric acid.

7. The gas adsorbent according to claim 1, wherein the weakly basic anion exchange resin is OH form.

8. A cigarette filter which comprises the gas adsorbent according to claim 1.

* * * * *